(12) United States Patent
Tarumi

(10) Patent No.: US 7,131,344 B2
(45) Date of Patent: Nov. 7, 2006

(54) DEVICE AND METHOD FOR INSPECTING INSIDE OF UNDERGROUND PIPE LINE AND METHOD OF INSPECTING CONCRETE ON INSIDE OF UNDERGROUND PIPE LINE FOR DETERIORATION

(75) Inventor: Minoru Tarumi, Nishinomiya (JP)

(73) Assignee: Burn-Am Co., Ltd., Amagasaki (JP)

( * ) Notice: Subject to any disclaimer, the term of this patent is extended or adjusted under 35 U.S.C. 154(b) by 61 days.

(21) Appl. No.: 10/506,607

(22) PCT Filed: Jul. 22, 2002

(86) PCT No.: PCT/JP02/07376

§ 371 (c)(1),
(2), (4) Date: Sep. 10, 2004

(87) PCT Pub. No.: WO03/076916

PCT Pub. Date: Sep. 18, 2003

(65) Prior Publication Data
US 2005/0115337 A1 Jun. 2, 2005

(30) Foreign Application Priority Data
Mar. 13, 2002 (JP) ............................. 2002-068625
May 7, 2002 (JP) ............................. 2002-131825

(51) Int. Cl.
*G01M 19/00* (2006.01)
(52) U.S. Cl. .................................................... 73/865.8
(58) Field of Classification Search ................ 73/865.8
See application file for complete search history.

(56) References Cited

U.S. PATENT DOCUMENTS

| | | | | |
|---|---|---|---|---|
| 3,718,978 A | * | 3/1973 | Van Koevering et al. ..... 33/544 |
| 3,964,171 A | * | 6/1976 | Gambini et al. ........... 33/544.2 |
| 4,986,314 A | * | 1/1991 | Himmler ..................... 138/97 |
| 5,331,578 A | * | 7/1994 | Stieler .......................... 702/93 |
| 5,392,715 A | * | 2/1995 | Pelrine ..................... 104/138.2 |

FOREIGN PATENT DOCUMENTS

| | | |
|---|---|---|
| EP | 484701 A1 * | 5/1992 |
| JP | 64-54216 | 3/1989 |
| JP | 2-59649 | 2/1990 |
| JP | 3-235084 | 10/1991 |
| JP | 4-136703 | 5/1992 |
| JP | 7-35152 | 2/1995 |
| JP | 7-311022 | 11/1995 |

(Continued)

*Primary Examiner*—Hezron Williams
*Assistant Examiner*—John Fitzgerald
(74) *Attorney, Agent, or Firm*—Amstrong, Kratz, Quintos, Hanson & Brooks, LLP

(57) ABSTRACT

A device for inspecting the inside of an underground pipe line which makes it possible to search for cavities on the outside of the underground pipe over the entire internal peripheral surface of the underground pipe, that is, not only upward of the underground pipe, but also toward both sides and downward thereof, to obtain detailed images of the inner peripheral surface of the pipe line without using a complex mechanism, and to display patterns of cracks and irregularities on the inner peripheral surface of the underground pipe by three-dimensional convergence images. The device comprises a pipe line internal self-propelled vehicle and an on-ground control unit, and the pipe line internal self-propelled vehicle is provided with a radar antenna, a camera equipped with a fisheye lens, a gyro, a laser sensor, and an infrared encoder.

14 Claims, 18 Drawing Sheets

FOREIGN PATENT DOCUMENTS

| | | |
|---|---|---|
| JP | 8-178907 | 7/1996 |
| JP | 9-61421 | 3/1997 |
| JP | 9-254782 | 9/1997 |
| JP | 10-2969 | 1/1998 |

* cited by examiner (a)

(b)

(a)

(b)

(a)

(b)

DEVICE AND METHOD FOR INSPECTING INSIDE OF UNDERGROUND PIPE LINE AND METHOD OF INSPECTING CONCRETE ON INSIDE OF UNDERGROUND PIPE LINE FOR DETERIORATION

TECHNICAL FIELD

The present invention relates to a device for inspecting the inside of an underground pipe line in an underground pipe embedded in the ground, inspection method therefor, and a method for inspecting concrete deterioration inside an underground pipe line of an underground pipe made from concrete.

BACKGROUND ART

Underground pipes that are buried in the ground and used for sewers and the like can cause environmental problems such as caving of roads or leakage of sewage due to cavities in the ground surrounding the underground pipe that occurred when the pipe was buried and cracks or fractures in the underground pipe that appeared thereafter. The state of the underground pipe lines has to be inspected to prevent such problems effectively. Devices designed to be employed for such an inspection have been suggested and used. A cavity inspection device using a pipe line internal self-propelled vehicle that is equipped with a radar is described in Japanese Patent Application Laid-open No. H10-2969 as a device for examining cavities present in the ground around an underground pipe from inside the pipe line of the underground pipe. Further, a device for taking pictures of the inner peripheral surface of a pipe line, which used a pipe line internal self-propelled vehicle carrying a camera, has been used as a device for examining cracks or fractures in the underground pipe after it has been buried, the examination being conducted from inside the pipe line of the underground pipe.

However, in the aforementioned cavity inspection device, the radar search is conducted only upward of the underground pipe and search toward both sides and downward of the underground pipe is not an object. However, a search conducted only upward of the underground pipe is insufficient for preventing caving of roads, and a search toward both sides and downward of the underground pipe is also necessary. Furthermore, in the device for taking pictures of the inner peripheral surface of a pipe line, the camera is usually fixed in the forward direction or rotated along the inner peripheral surface. However, when the camera is fixed, a detailed image is difficult to obtain, and rotating the camera requires a complex mechanism. Further, devices designed to display cracks or pattern of irregularities on the inner peripheral surface of a pipe line with a three-dimensional convergence image have not been found.

In concrete underground sewers, hydrogen sulfide contained in sewage is converted into sulfuric acid by sulfur oxidizing bacteria, and this sulfuric acid reacts with cement components contained in the concrete and is converted into gypsum dehydrate, thereby causing concrete embrittlement. The embrittled portions have to be removed, for which purpose the concrete of the inner peripheral surface of the sewer has to be sampled and analyzed, this operation being costly and troublesome. Moreover, the analysis requires about 10 days.

Further, because the cavity inspection device using a pipe line internal self-propelled vehicle has a large size, inspection of underground pipes of small diameter, such as lateral sewers connected from the ground surface to the main sewer pipe, is difficult to conduct by employing such a large cavity inspection devices using a pipe line internal self-propelled vehicle.

With the foregoing in view, it is an object of the present invention to provide a device for inspecting the inside of an underground pipe line that makes it possible to search for cavities on the outside of the underground pipe over the entire internal peripheral surface of the underground pipe, that is, not only upward of the underground pipe, but also toward both sides and downward thereof, to obtain detailed images of the inner peripheral surface of the pipe line, without using a complex mechanism, and to display patterns of cracks and irregularities on the inner peripheral surface of the underground pipe by three-dimensional convergence images. Another object is to provide a device for inspecting the inside of an underground pipe line that can easily judge the presence or absence of concrete deterioration inside underground sewers made from concrete and a method therefor. Yet another object is to provide a device for inspecting the inside of an underground pipe line that can be used for inspecting underground pipes of a small diameter, such as lateral sewers, which are connected from the ground surface to the main sewer pipe, and an inspection method using such device.

DISCLOSURE OF THE INVENTION

The first device for inspecting the inside of an underground pipe line comprises a pipe line internal self-propelled vehicle, which comprises a radar antenna and travels inside the pipe line of the underground pipe, and an on-ground control unit for conducting control of the movement of the pipe line internal self-propelled vehicle and processing signals of the radar, wherein the pipe line internal self-propelled vehicle comprises an antenna rotation mechanism for rotating the antenna along the inner peripheral surface of the underground pipe and capable of changing the position of the antenna so that the antenna follows the inner peripheral surface. With the first device for inspecting the inside of an underground pipe line, the position of the antenna of the radar for inspecting cavities present in the ground surrounding the underground pipe can be varied according to the inner diameter of the underground pipe, so as to become optimum for measurements, and this position can be adapted for inspecting the underground pipes of different inner diameters. Further, because the antenna rotates along the inner peripheral surface of the underground pipe, search for cavities on the outside of the underground pipe can be conducted over the entire inner peripheral surface of the underground pipe, that is, not only upward of the underground pipe, but also toward both sides and downward thereof.

As the second device for inspecting the inside of an underground pipe line, in the above-described device for inspecting the inside of an underground pipe line, the pipe line internal self-propelled vehicle comprises a height adjustment mechanism capable of changing the position of the antenna rotation mechanism in the up-down direction inside the pipe line of the underground pipe according to the inner diameter of the underground pipe so that the rotation center of the antenna coincides with the center of the inner diameter of the underground pipe. With such second device for inspecting the inside of an underground pipe line, the rotation center of the antenna is aligned with the center of the inner diameter of the underground pipe. Therefore, uniform search for cavities can be conducted over the entire inner peripheral surface of the underground pipe.

As the third device for inspecting the inside of an underground pipe line, in the above-described device for inspecting the inside of an underground pipe line, the pipe line internal self-propelled vehicle may comprise antenna position detection means for detecting the position of the antenna, and in the on-ground control unit, signals of the radar may be analyzed and radar images of the ground surrounding the underground pipe in a plurality of directions perpendicular to the traveling direction of the pipe line internal self-propelled vehicle may be created as two-dimensional radar images for each direction and displayed in a real time mode.

Here, the two-dimensional radar image is a diagram plotted by analyzing the radar signal, where the traveling direction of the pipe line internal self-propelled vehicle, that is, the distance in the axial direction of the underground pipe, serves as an abscissa and the distance outward of the inner peripheral surface of the underground pipe line serves as an ordinate. With the third device for inspecting the inside of an underground pipe line, it is possible to create two-dimensional radar images in a plurality of directions outward of the inner peripheral surface of the underground pipe, that is, in a plurality of directions perpendicular to the traveling direction of the pipe line internal self-propelled vehicle. Further, because the pipe line internal self-propelled vehicle is provided with the antenna position detection means for detecting the position of the antenna, the actual search direction in searching for cavities in the ground around the underground pipe can be accurately associated with a two-dimensional radar image obtained by analyzing the radar signals and the search for cavities can be conducted with good accuracy.

In the above-described device for inspecting the inside of an underground pipe line, the antenna was rotated along the inner peripheral surface inside the pipe line of the underground pipe, but sometimes only the zone in the ground above the ceiling of the pipe line may be selected as a cavity inspection object. The fourth device for inspecting the inside of an underground pipe line, which is designed for such cases, is a device for inspecting the inside of an underground pipe line, which is provided with a radar for inspecting cavities present in at least part of the ground surrounding the underground pipe, this device comprising a pipe line internal self-propelled vehicle, which comprises a radar antenna and travels inside the pipe line of the underground pipe, and an on-ground control unit for conducting control of the movement of the pipe line internal self-propelled vehicle and processing signals of the radar, wherein the pipe line internal self-propelled vehicle comprises a parallel link mechanism for supporting the antenna positioned above the pipe line internal self-propelled vehicle, so that the antenna can be lifted or lowered according to the height of the ceiling inside the pipe line of the underground pipe. With the fourth device for inspecting the inside of an underground pipe line, the mechanism can be simplified with respect to that in which the antenna is rotated along the inner peripheral surface of the pipe line of the underground pipe.

As the fifth device for inspecting the inside of an underground pipe line, in the above-described device for inspecting the inside of an underground pipe line, respective linkages of the parallel link mechanism can have a variable length and can be extended or contracted, and the upper surface of the antenna can be tilted forward and backward so as to follow the shape of the ceiling. With the fifth device for inspecting the inside of an underground pipe line, the upper surface of the antenna can follow the ceiling shape and the accuracy of inspection can be improved.

As the sixth device for inspecting the inside of an underground pipe line, in the above-described device for inspecting the inside of an underground pipe line, the pipe line internal self-propelled vehicle may comprise a fisheye lens camera for taking the pictures of the inner peripheral surface of the underground pipe line in front of the vehicle in the traveling direction and the expanded image may be created and displayed in a real time mode by the on-ground control unit from the images picked up with the fisheye lens camera. Here, the expanded image is a detailed plane image of the inner peripheral surface of the underground pipe created by converting the images of the inner peripheral surface of the underground pipe line that were picked up with the fisheye lens camera, where the traveling direction of the pipe line internal self-propelled vehicle, that is, the distance in the axial direction of the underground pipe, serves as an abscissa and the distance outward of the inner peripheral surface of the underground pipe line serves as an ordinate. With the sixth device for inspecting the inside of an underground pipe line, there is fixedly provided a fisheye lens camera for taking pictures of the inner peripheral surface of the underground pipe line and an expanded image is created from the images picked up with the fisheye lens camera. Therefore, the detailed expanded image of the inner peripheral surface of the underground pipe can be obtained and cracks or fractures of the underground pipe can be detected without using a complex mechanism for rotating the camera.

As the seventh device for inspecting the inside of an underground pipe line, in the above-described device for inspecting the inside of an underground pipe line, the pipe line internal self-propelled vehicle may comprise a gyro for measuring the inclination of the pipe line internal self-propelled vehicle in the traveling direction with respect to the horizontal direction and a laser sensor for rotating along the inner peripheral surface of the underground pipe to measure the convergence of the underground pipe over the entire inner peripheral surface, and the signals of the gyro and the signals of the laser sensor may be analyzed in the on-ground control unit to create three-dimensional convergence images and display them in a real time mode. Here, the convergence refers to the shape of the inner periphery of the underground pipe, and the three-dimensional convergence image is an image obtained by selecting an X axis as the traveling direction of the pipe line internal self-propelled vehicle, that is, the distance in the axial direction of the underground pipe, an Y axis as the horizontal direction of a circle formed by inner periphery of the underground pipe, and Z axis as the vertical direction to this circle, plotting the X axis, Y axis, and Z axis on a plane, and plotting on the same plane the shape of the inner periphery of the underground pipe intermittently along the axial direction of the underground pipe, while reflecting the inclination of the underground pipe line obtained from the analysis of the gyro signals. With the seventh device for inspecting the inside of an underground pipe line, the inclination of the underground pipe line or cracks or a peak-valley pattern on the inner peripheral surface of the pipe line can be displayed as a three-dimensional convergence image and deformations of the inner portions of the underground pipe or cracks and fractures thereof can be detected.

As the eighth device for inspecting the inside of an underground pipe line, in the above-described device for inspecting the inside of an underground pipe line, in the on-ground control unit, the correspondence may be established between the radar image and the expanded image in the same observation point or, when the convergence image is present, the correspondence may be established between the radar image, the expanded image and the convergence image. With the eighth device for inspecting the inside of an underground pipe line, it is possible to establish the correspondence between the radar image and the expanded image of the same observation point and, when the convergence image is present, to establish the correspondence between the radar image, expanded image and convergence image. Therefore, the position in which a cavity is present can be reliably determined by establishing the correspondence between the position of a specific image on the expanded image or convergence image and the position where the cavity is present on the radar image. Alternatively, the deformations of the inner portions of the underground pipe or the positions where cracks and fractures of the underground pipe are present can be reliably determined by establishing the correspondence between the expanded image and the convergence image.

As the ninth device for inspecting the inside of an underground pipe line, in the above-described device for inspecting the inside of an underground pipe line, the pipe line internal self-propelled vehicle may comprise an infrared encoder for measuring the travel distance thereof. With the ninth device for inspecting the inside of an underground pipe line, the distance from the inspection start point of the underground pipe line to the inspection position can be accurately measured and the positions where the cavities or deformations, cracks, and fractures of the underground pipe are present can be reliably determined from the distance from the inspection start point to the position where the cavities or deformations, cracks, and fractures of the underground pipe are present by establishing the correspondence between this distance and each of the above-described image.

The tenth device for inspecting the inside of an underground pipe line with the object of detecting the presence of concrete deterioration inside a sewage pipe made from concrete will be described below. In the tenth device for inspecting the inside of an underground pipe line, the pipe line internal self-propelled vehicle comprises a fisheye lens camera for taking the pictures of the inner peripheral surface of the underground pipe line forward in the traveling direction and the expanded image is created and displayed in a real time mode by the on-ground control unit from the images picked up with the fisheye lens camera, wherein the pipe line internal self-propelled vehicle comprises spraying means for spraying a concrete deterioration diagnostic reagent, which changes the color of the surface to which it has adhered according to the presence or absence of concrete deterioration, on the inner peripheral surface of the concrete in the underground pipe line when the self-propelled vehicle travels inside the pipe line. With the tenth device for inspecting the inside of an underground pipe line, for example, a concrete deterioration diagnostic reagent, which colors the surface to which it has adhered into different colors depending on whether concrete deterioration is present or not, can be sprayed on the inner peripheral surface of the concrete in the underground pipe line when the self-propelled vehicle travels forward and the results can be picked up with the fisheye lens camera when the self-propelled vehicle moves backward. Therefore, the presence of concrete deterioration in the underground pipe line can be judged by the image picked up with the camera.

When the underground pipe line is a sewage pipe, hydrogen sulfide contained in sewage is converted into sulfuric acid by sulfur oxidizing bacteria and concrete easily deteriorates under the effect of the sulfuric acid. Therefore, it is recommended that a reagent for judging the presence of deterioration caused by sulfuric acid be used as the concrete deterioration diagnostic reagent in the eleventh device for inspecting the inside of an underground pipe line.

The twelfth device for inspecting the inside of an underground pipe line may comprise a sensor for detecting toxic gases such as hydrogen sulfide in order to inspect the presence of toxic gases such as hydrogen sulfide simultaneously with the inspection of the underground pipe line in above-described device for inspecting the inside of an underground pipe line.

As the thirteenth device for inspecting the inside of an underground pipe line, the above-described device for inspecting the inside of an underground pipe line may be provided with a function of establishing the correspondence between the gyro and the laser sensor, or the radar image and the expanded image described hereinabove. Thus, such a device for inspecting the inside of an underground pipe line comprises a gyro for measuring the inclination of the pipe line internal self-propelled vehicle in the traveling direction with respect to the horizontal direction and a laser sensor for rotating along the inner peripheral surface of the underground pipe to measure the convergence of the underground pipe over the entire inner peripheral surface, and the signals of the gyro and the signals of the laser sensor are analyzed in the on-ground control unit to create three-dimensional convergence images and display them in a real time mode.

As the fourteenth device for inspecting the inside of an underground pipe line, in the on-ground control unit of the above-described device for inspecting the inside of an underground pipe line, the correspondence is established between the radar image and the expanded image in the same observation point or, when the convergence image is present, the correspondence is established between the radar image, the expanded image and the convergence image in the same observation point.

Further, as the fifteenth device for inspecting the inside of an underground pipe line, the above-described device for inspecting the inside of an underground pipe line comprises an infrared encoder for measuring the travel distance thereof.

Further, a method for inspecting the deterioration of concrete inside an underground pipe line by using the above-described device for inspecting the inside of an underground pipe line, which comprises spraying means for spraying a concrete deterioration diagnostic reagent, is a method as follows. Thus, the spraying means sprays a concrete deterioration diagnostic reagent, which changes the color of the surface to which it has adhered according to the presence or absence of concrete deterioration, on the inner peripheral surface of the concrete in the underground pipe line when the self-propelled vehicle moves inside the pipe line, after the spraying, the fisheye lens camera takes pictures of the inner peripheral surface of the underground pipe line, and the on-ground control unit creates the expanded image from the picked-up images, judges as to whether the deterioration of the inner peripheral surface of the concrete is present based on the expanded image, and displays them in a real time mode.

The sixteenth device for inspecting the inside of an underground pipe line that can be used for inspecting underground pipes with a small diameter, such as lateral sewers connected from the ground surface to the main sewer pipe. With the sixteenth device for inspecting the inside of an underground pipe line, the component carrying the radar and used by insertion into the pipe line of the underground pipe that is the subject of the inspection is miniaturized, the component can be inserted into a lateral sewer of a small diameter, the component carrying the radar is rotated inside the pipe line of the lateral sewer by rotating the cable around its axis on the ground, while maintaining the integrity of the component carrying the radar and the cable connected to this component, and the lateral sewer can be inspected over the entire perimeter.

More specifically, the sixteenth device for inspecting the inside of an underground pipe line is composed of an inspection unit, an on-ground control unit, and a cable. The inspection unit has a cylindrical body for insertion into the pipe line of the underground pipe, wherein a radar is provided inside the body so that the electromagnetic waves thereof are emitted unidirectionally from the outer peripheral surface of the body toward the inner peripheral surface of the underground pipe. The on-ground control unit processes signals of the radar. The cable is covered with a flexible tube having flexibility, the base end of the cable is connected to the on-ground control unit and the other end thereof is coupled to the rear end of the inspection unit coaxially with the inspection unit. The inspection unit is moved forward or backward inside the pipe line of the underground pipe by pushing or pulling the flexible tube on the ground, and if the flexible tube is rotated about its axis on the ground, this rotation is transferred to the inspection unit via the flexible tube and the inspection unit rotates inside the pipe line of the underground pipe about the axis thereof.

As the seventeenth device for inspecting the inside of an underground pipe line, in the above-described device for inspecting the inside of an underground pipe line, supporters providing for smooth contact between the inspection unit and the inner peripheral surface when the inspection unit moves forward or backward or rotated about the axis thereof are provided on the outer peripheral surface of the inspection unit.

In the eighteenth device for inspecting the inside of an underground pipe line, the degree of protrusion of the supporters from the outer peripheral surface changes according to changes in the inner diameter of the underground pipe, so that the top portions of the supporters are in contact with the inner peripheral surface of the underground pipe.

As the nineteenth device for inspecting the inside of an underground pipe line, in the above-described device for inspecting the inside of an underground pipe line, the base end of the cable is connected to the on-ground control unit via a cable winding unit for winding up the cable, and the cable winding unit is provided with a rotary mechanism which rotates the flexible tube covering the cable about its axis.

As the twentieth device for inspecting the inside of an underground pipe line, in the above-described device for inspecting the inside of an underground pipe line, the inspection unit is provided with a gyro for measuring the rotation axis direction and rotation angle of the inspection unit when the inspection unit rotates about its axis.

As the twenty first device for inspecting the inside of an underground pipe line, the above-described device for inspecting the inside of an underground pipe line preferably comprises an encoder for on-ground measurements of the draw-out length of the cable in the insertion direction when the inspection unit is inserted into the pipe line of the underground pipe.

Further, as the twenty second device for inspecting the inside of an underground pipe line, in the above-described device for inspecting the inside of an underground pipe line, a fisheye lens camera for taking the pictures of the inner peripheral surface of the pipe line of the underground pipe forward in the insertion direction may be provided at the front end of the inspection unit and an expanded image may be created and displayed in a real time mode by the on-ground control unit from the images picked up with the fisheye lens camera. Here, the expanded image, as described hereinabove, is a detailed plane image of the inner peripheral surface of the underground pipe created by converting the images of the inner peripheral surface of the underground pipe line that were picked up with the fisheye lens camera, where the distance in the traveling direction of the inspection unit serves as an abscissa and the inner periphery of the underground pipe line serves as an ordinate.

The method for inspecting the inside of an underground pipe line by using the above-described device for inspecting the inside of an underground pipe line is the method as follows. Thus, the distance traveled by the inspection unit inside the pipe line of the underground pipe is found by the draw-out length of the cable in the insertion direction and the position in which the inspection unit is located inside the pipe line is recognized, and the inspection unit is rotated inside the pipe line of the underground pipe by rotating the flexible tube covering the cable about its axis and cavities present in the ground surrounding the underground pipe are inspected over the entire periphery of the underground pipe.

BEST MODE FOR CARRYING OUT THE INVENTION

Figure 1:
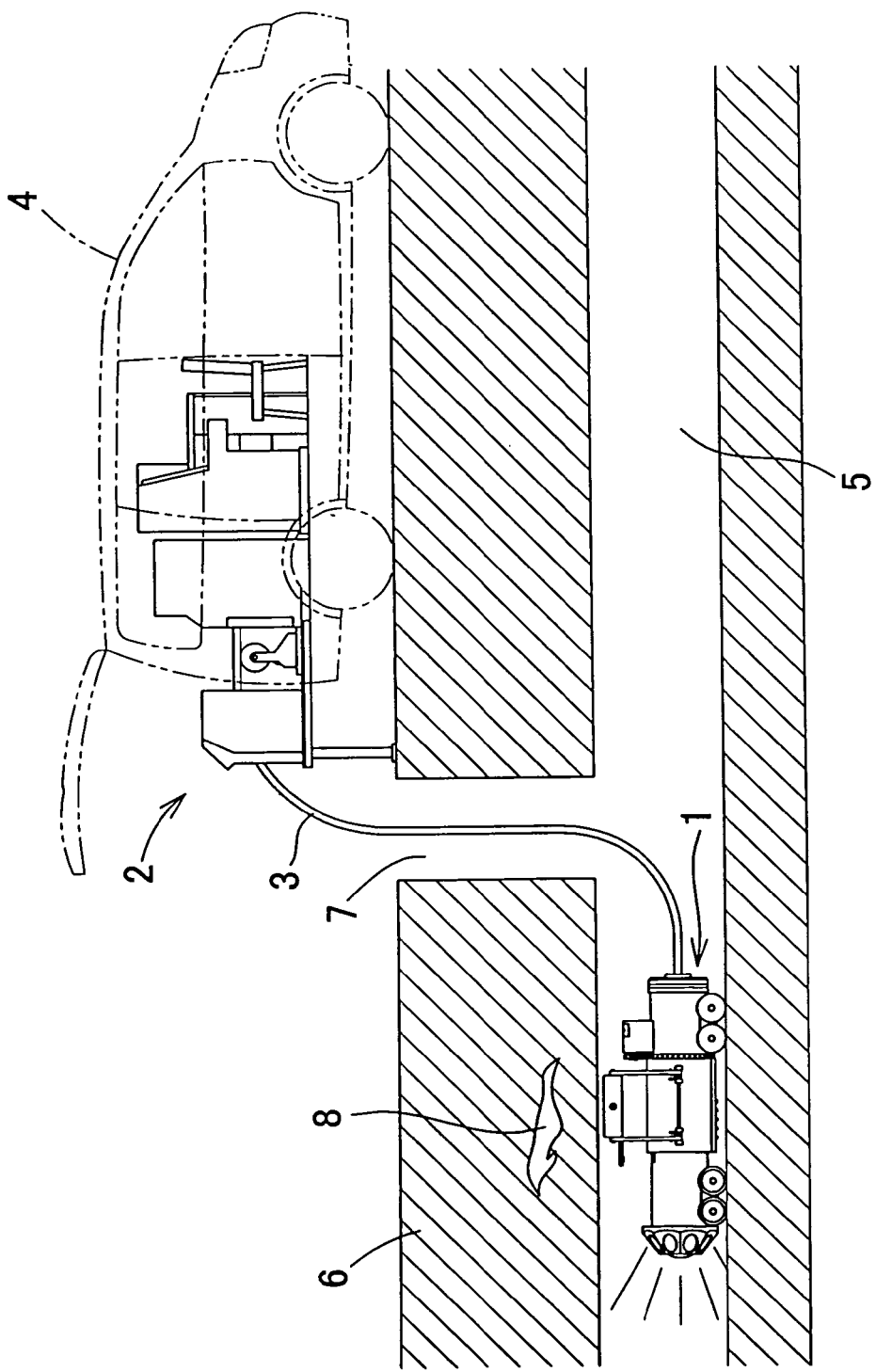
FIG. 1 shows the configuration of the device for inspecting the inside of an underground pipe line of the first embodiment.

The embodiments of the present invention will be described hereinbelow with reference to the appended drawings. FIG. 1 shows the configuration of the device for inspecting the inside of an underground pipe line of the first embodiment. Referring to FIG. 1, the device for inspecting the inside of an underground pipe line of the first embodiment comprises a pipe line internal self-propelled vehicle 1 and an on-ground control unit 2. The device for inspecting the inside of an underground pipe line is used by inserting the pipe line internal self-propelled vehicle 1 from a manhole 7 into the underground pipe line 5 of an underground pipe embedded in a ground 6 and conducting the inspection of the underground pipe line 5 or the inspection of cavities 8 present in the ground surrounding the underground pipe line. The on-ground control unit 2 is carried on an on-ground control unit vehicle 4 and connected to the pipe line internal self-propelled vehicle 1 with a cable 3. The control unit controls the movement of the pipe line internal self-propelled vehicle 1, receives and processes various signals generated from the pipe line internal self-propelled vehicle 1, and then outputs them to a printer and shows on a display as image information. The inspection of the underground pipe line 5 or the inspection of cavities present in the ground surrounding the underground pipe is conducted based on this image information.

Figure 2:
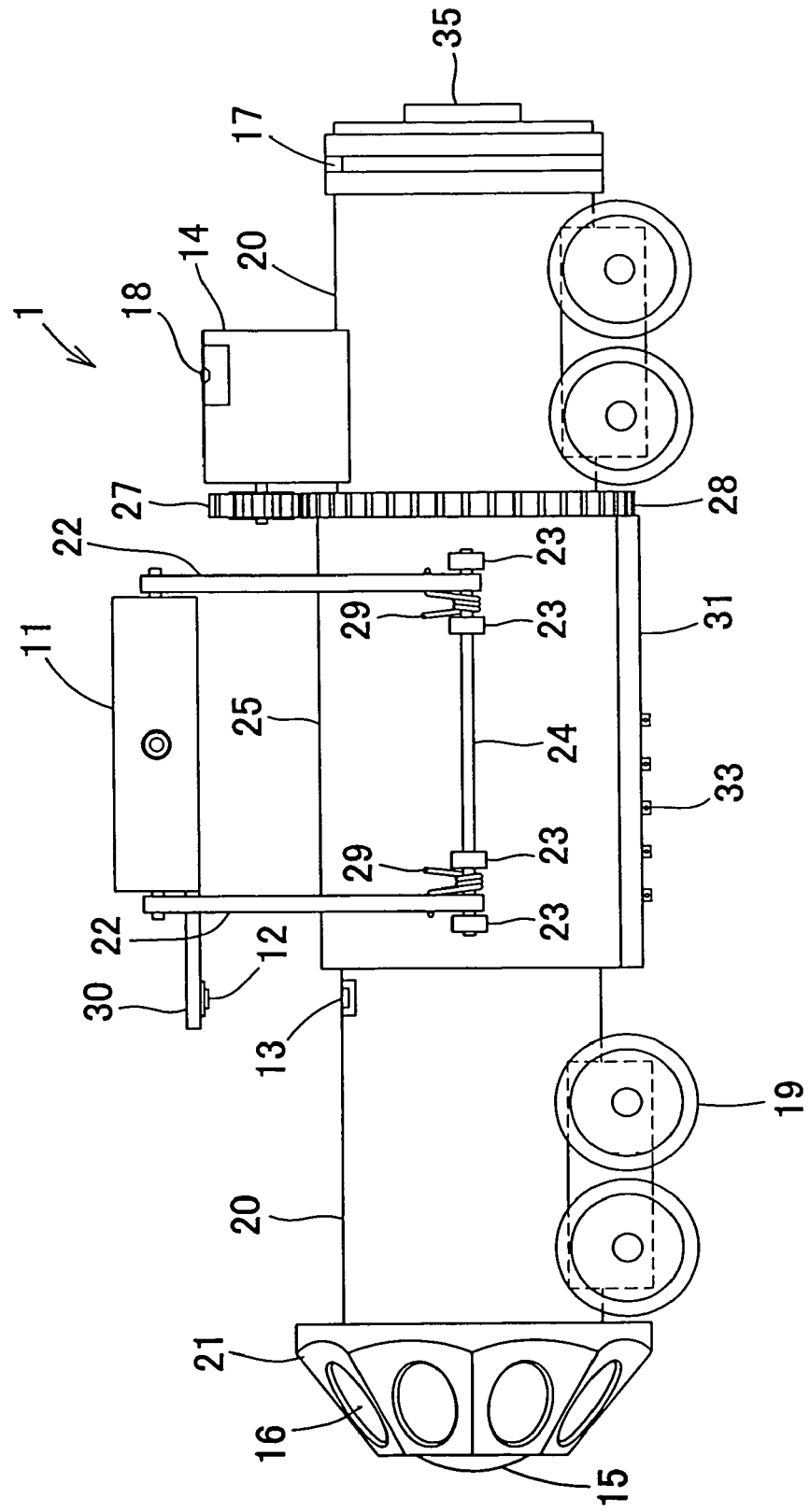
FIG. 2 is a side view of the pipe line internal self-propelled vehicle of the first embodiment.

The configuration of the pipe line internal self-propelled vehicle 1 will be described below. FIG. 2 is a side view of the pipe line internal self-propelled vehicle. FIG. 3(a) is a front view illustrating a case in which the pipe line internal self-propelled vehicle 1 was inserted into a large-diameter underground pipe 9. FIG. 3(b) a front view illustrating a case in which the pipe line internal self-propelled vehicle 1 was inserted into a small-diameter underground pipe 9. The pipe line internal self-propelled vehicle 1 comprises, as the main equipment components, wheels 19 mounted on a cylindrical body casing of the pipe line internal self-propelled vehicle 1, a motor (not shown in the figures) for driving the wheels 19 under control from the on-ground control unit 2, a radar antennal 11 for rotating around the body casing 20 in order to conduct the inspection of cavities 8 in the ground surrounding the underground pipe 9, a camera (not shown in the figure) installed inside the body casing 20 and comprising a fisheye lens 15 provided in the head portion of the body casing 20 for detecting cracks or fractures in the underground pipe, an illumination lamp 16 for the fisheye lens camera provided in the head portion of the body casing 20 so as to surround the fisheye lens 15, a laser gyro (not shown in the figures) provided inside the body casing 20 for measuring the inclination of the pipe line internal self-propelled vehicle 1 in the traveling direction with the object of measuring the inclination of the axial direction of the underground pipe line with respect to the horizontal direction and a laser sensor provided in the end portion of the pipe line internal self-propelled vehicle 1 for measuring the variations of the inner space of the underground pipe, and an infrared encoder 18 for measuring the distance traveled by the pipe line internal self-propelled vehicle 1.

Figure 4:
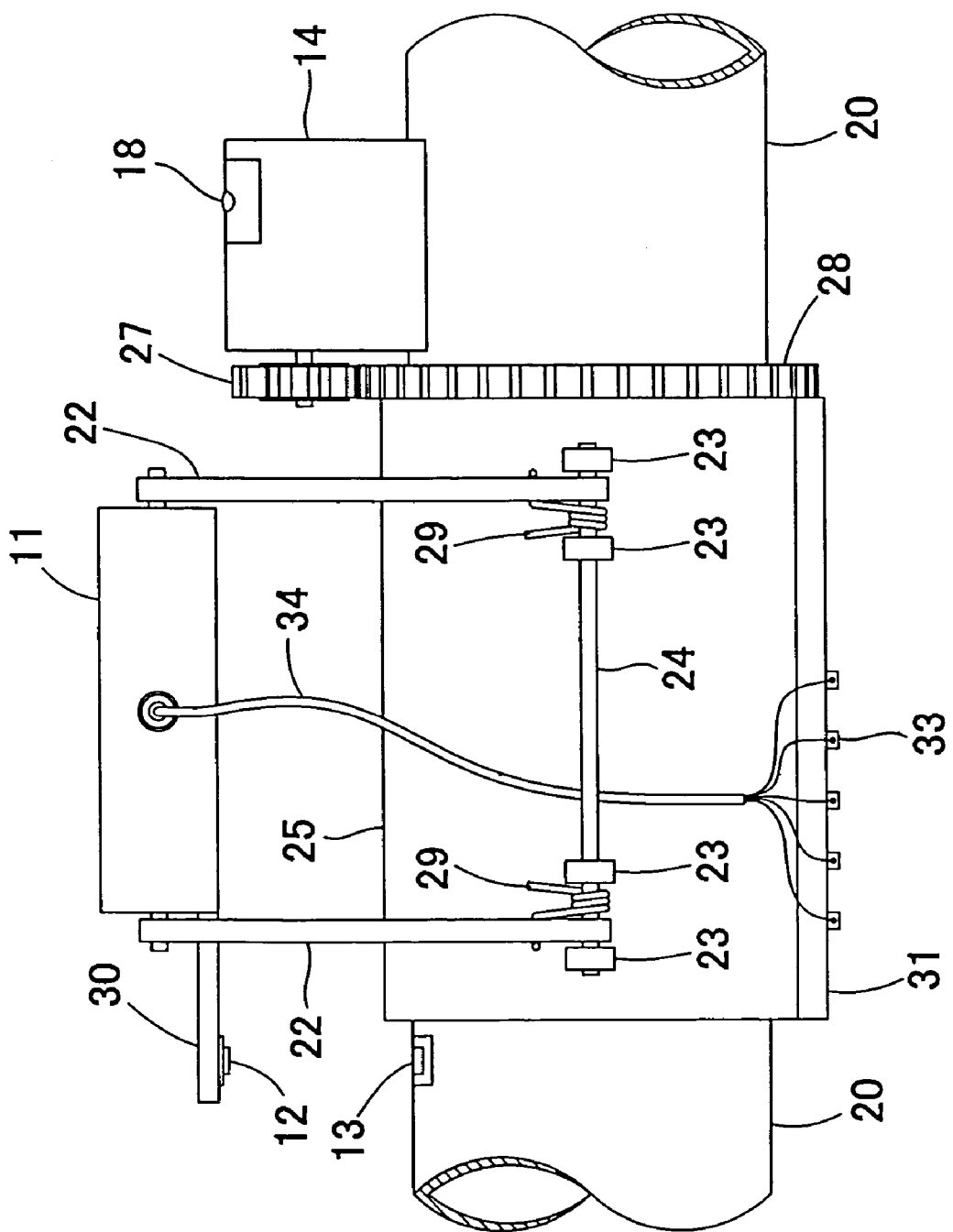
FIG. 4 is a side view illustrating the components of the rotation mechanism of the radar antenna of the pipe line internal self-propelled vehicle of the first embodiment.
Figure 5:
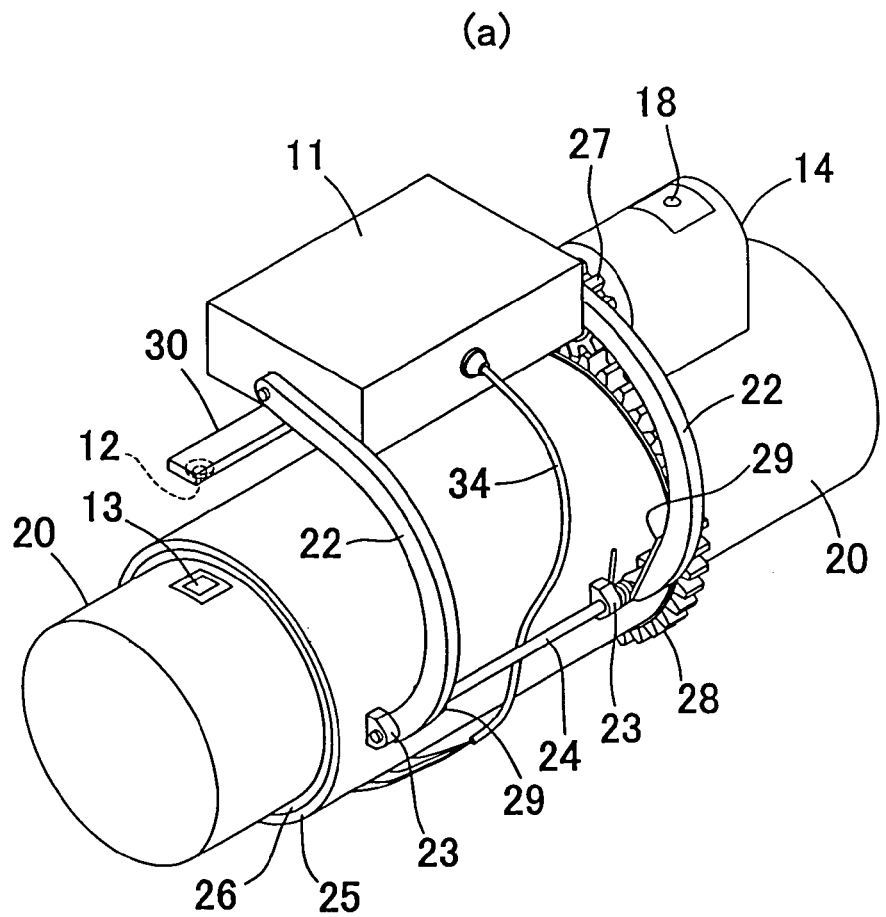
FIG. 5(a) is a perspective view illustrating the components of the rotation mechanism of the radar antenna of the pipe line internal self-propelled vehicle of the first embodiment; figure (b) is a perspective view illustrating part of the configuration shown in figure (a).
Figure 5:
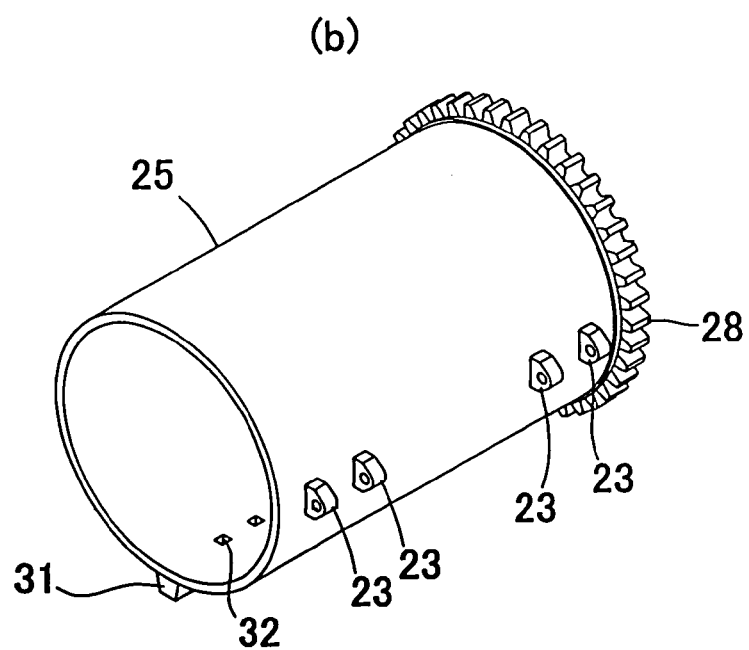

The radar antenna 11 provided at the pipe line internal self-propelled vehicle 1 will be described below. As mentioned hereinabove, the radar antenna 11 rotates around the body casing 20. FIG. 4 is a side view of the mechanical components thereof. FIG. 5(a) is a perspective view thereof, and FIG. 5(b) is a part of the view shown in FIG. 5(a). Distal ends of two shaped antenna support arms 22 holding the radar antenna 11 at the base ends thereof are fixed by using an antennal support arm fixing rod 24 to an antenna support arm fixing piece 23 provided on the surface of an outer sleeve 25 which slips and rotates around an inner sleeve 26 provided around the cylindrical body casing 20. An outer sleeve rotation gear 28, which is a ring-like gear engaged with an antenna drive motor gear directly linked to the antenna drive motor 14, is provided on the ring-like side surface of the outer sleeve 25. The rotation of the antenna drive motor 14 rotates the outer sleeve 25 around the inner sleeve 26, thereby rotating the radar antenna 11 around the inner sleeve 26, that is, around the body casing 20.

When the radar antenna 11 is rotated along the inner peripheral surface of the underground pipe 9 with the object of inspecting cavities 8 present in the ground surrounding the underground pipe 9, the center of rotation is preferably the center of the inner periphery of the underground pipe 9. Accordingly, it is necessary to adjust the position of the body casing 20 in the up-down direction inside the underground pipe line 5. In the present embodiment, as shown in FIGS. 3(a) and (b), this adjustment is carried out by adjusting the distance between the wheels 19 mounted on the body casing 20. However, the adjustment method is not limited to the aforementioned method. Thus, a method based on employing a plurality of wheels of different diameters, a method of fitting the wheels with a large diameter on the outside of the wheels with a small diameter, or a method of employing a mechanism for separating the wheels and the body casing and adjusting the height therebetween may be used.

In the present embodiment, wheels in the form of a circular truncated cone that are narrowed to the outside are used as the wheels 19 with the object of stabilizing the movement of the pipe line internal self-propelled vehicle 1. Further, a laser gyro (not shown in the figures) is installed inside the pipe line internal self-propelled vehicle 1 to obtain the horizontal stature of the pipe line internal self-propelled vehicle 1 in the left-right direction with respect to the traveling direction.

Figure 3:
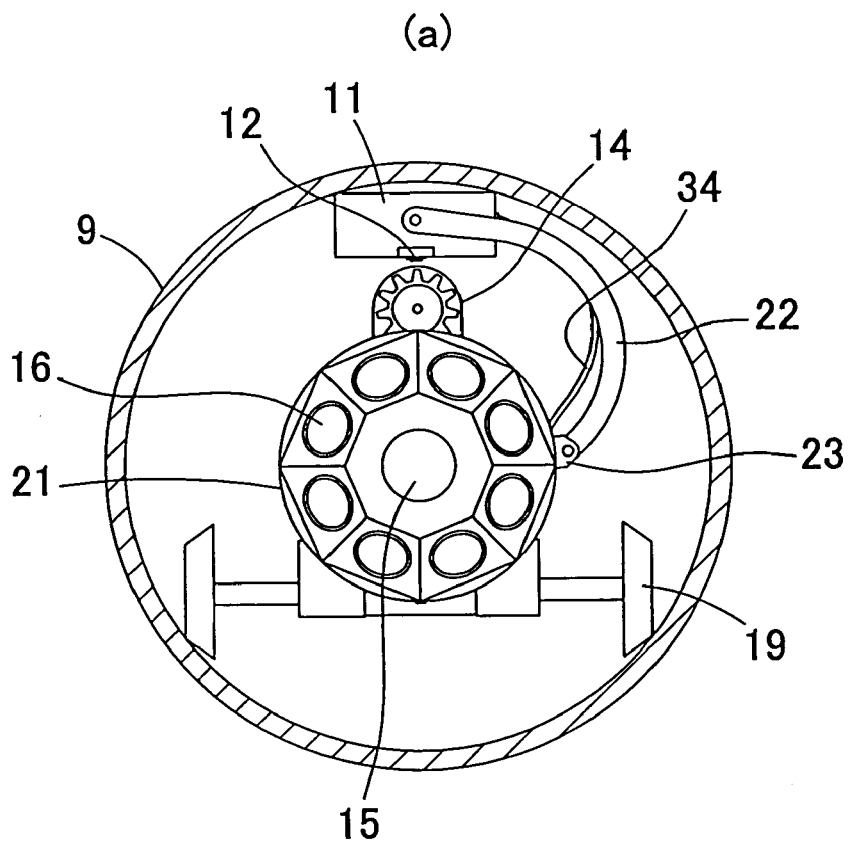
FIG. 3(a) is a front view illustrating a case in which the pipe line internal self-propelled vehicle of the first embodiment was inserted into a large-diameter underground pipe.
FIG. 3(b) a front view illustrating a case in which the pipe line internal self-propelled vehicle was inserted into a small-diameter underground pipe.
Figure 3:
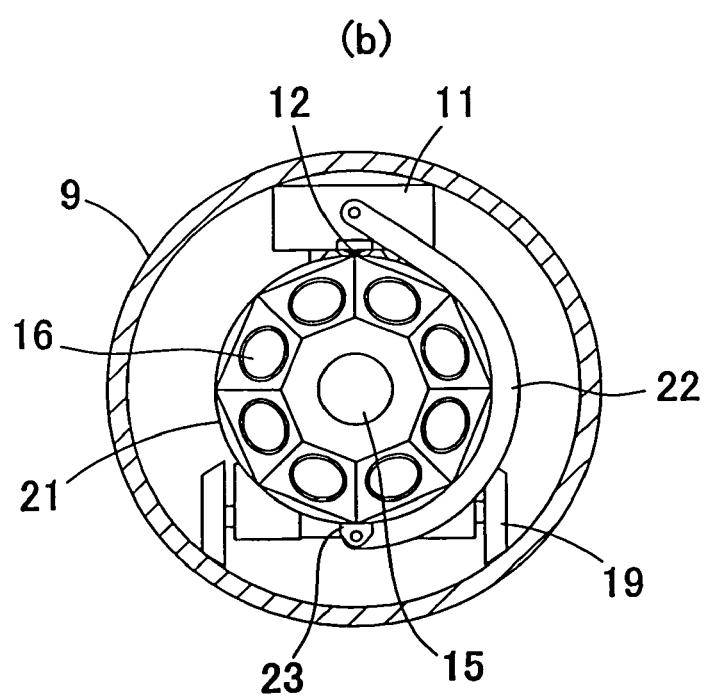

Furthermore, in order to inspect cavities 8 in the ground surrounding the underground pipe 9, the radar antenna 11 is preferably disposed as close as possible to the inner peripheral surface of the underground pipe 9. For this purpose, in the present embodiment, as shown in FIGS. 3(*a*) and (*b*), the respective adjustment is conducted by moving the antenna support arms 22 so that they are brought close to or withdrawn from the outer sleeve 25, that is, the body casing, where the antenna support arm fixing rod 24, which fixes the antenna support arm 22 to the antenna support arm fixing piece 23, serves as an axis. However, this method is not limiting and any method may be used, provided that the distance between the body casing 20 and the radar antenna 11 can be adjusted.

Further, in the present embodiment, the center of rotation of the radar antenna was the center of the inner periphery of the underground pipe 9. However, this is not the only possible configuration. For example, a method can be considered which uses a mechanism automatically providing for optimum distance between the body casing 20 and the radar antenna 11 along the inner periphery of the underground pipe 9, even when the center of rotations is shifted from the center of the inner periphery of the underground pipe 9.

Further, in the present embodiment, the radar antenna 11 is pressed against the inner peripheral surface of the underground pipe 9 by using a kick spring 29 shown in FIG. 4, so that the radar antenna is rotated in contact with the inner peripheral surface of the underground pipe 9.

Furthermore, it is necessary to determine accurately the position on the inner periphery of the underground pipe 9 where the electromagnetic waves of the radar antenna are reflected, that is, the position on the inner periphery of the underground pipe 9 where cavity inspection in the outward direction is conducted. Accordingly, a radar position detection sensor 12 composed of a light projector and a reflected light receiver is provided on the lower surface of the distal end portion of a radar position detection sensor mounting piece 30 protruding forward from the radar antenna 11, a radar position top portion mark 13 is provided in the top portion of the surface of the body casing 20 facing the radar position detection sensor 12, and the presence of the radar antenna 11 in the top portion on the inner periphery of the underground pipe 9 is detected by detecting the radar position top portion display mark 13 with the radar position detection sensor 12. Further, a position detection rotary encoder (not shown in the figure), which is linked to the outer sleeve 25 rotating integrally with the radar antenna 11 is provided inside the body casing 20, as means for detecting the position of the radar antenna outside the top portion of the inner periphery of the underground pipe 9. Further, if a mounting angle of the antenna support art 22 and outer sleeve 25 is temporarily fixed in order to held the above-described optimum position of the radar antenna 11 determined based on the inner diameter of the underground pipe 9, then the relationship between the reference position of the position detection rotary encoder and the detection position of the radar position top portion display mark 13 can be uniquely determined. Therefore, the position of the radar antenna 11 on the inner periphery of the underground pipe 9 can be found by computation based on the output signal of the position detection rotary encoder.

Further, the infrared encoder 18 is provided above the antenna rotation motor 14. As the pipe line internal self-propelled vehicle 1 moves, the infrared radiation is emitted from the infrared encoder 18 toward the inner peripheral surface of the underground pipe 9, and the distance traveled by the pipe line internal self-propelled vehicle 1 from the inspection initiation point is found by observing the reflected light.

Further, the signal outputted from the rotating radar antenna 11 has to be transmitted to the on-ground control unit 2. Here, a slip ring is provided on the surface of the inner sleeve 26, and a brush 33 made from carbon is fit into a brush fitting orifice 32 of the brush mounting portion 31 provided at the outer sleeve 25, so that the brush is brought into contact with the slip ring. A wire for the signal outputted from the radar antenna 11 is connected to the brush 33. Further, the signal wire which is conductively linked to the slip ring on the surface of the inner sleeve 26 is connected to the on-ground control unit 2 via a connector 35 for a connecting cable. In the first embodiment, the above-described mechanism is used to pick up the signals outputted from the rotating radar antenna 11.

Figure 6:
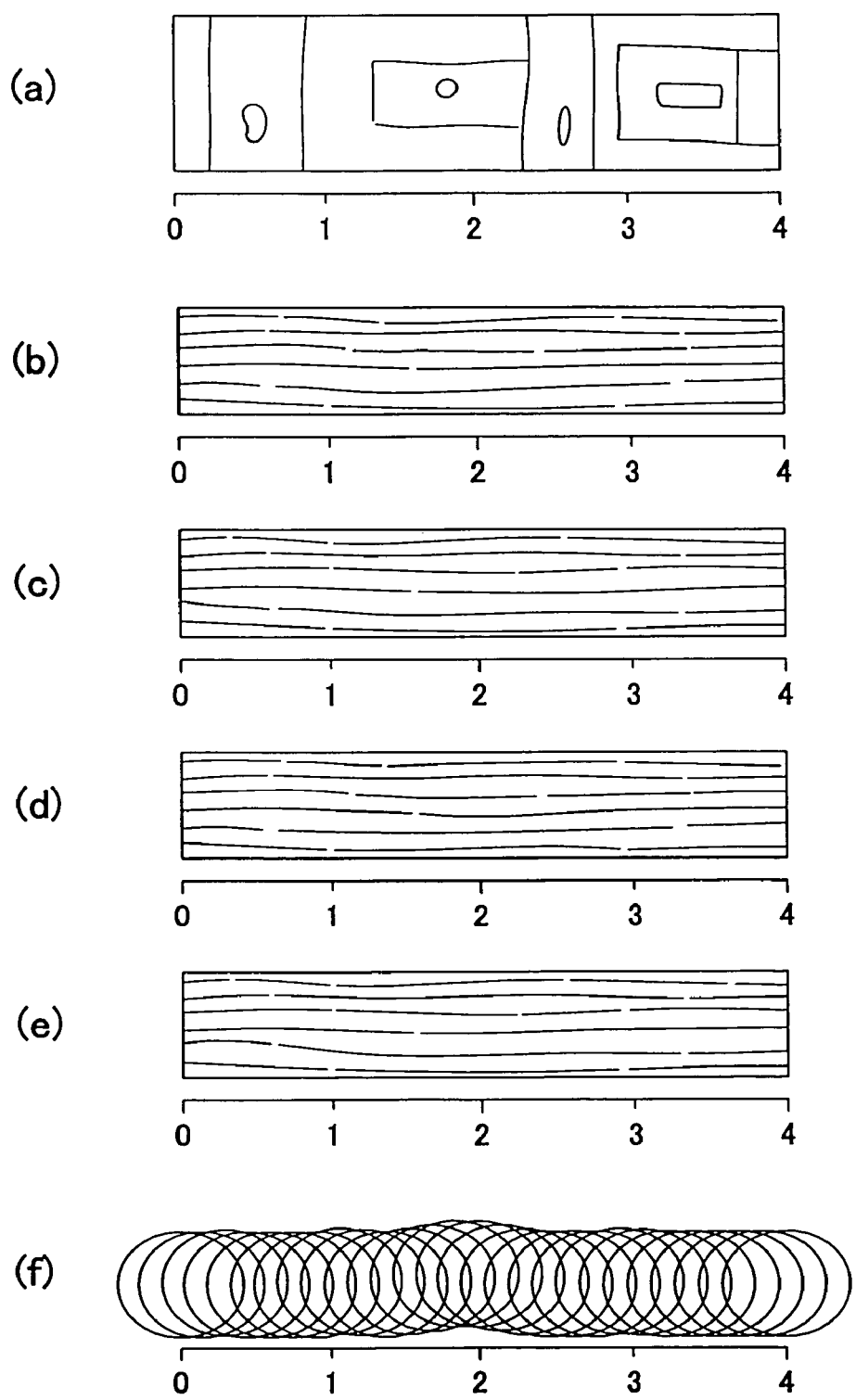
FIG. 6 is an explanatory drawing illustrating an example of the output of a printer of the on-ground control unit of the first embodiment; (a) shows an expanded image based on the images picked up by the fisheye lens camera, (b), (c), (d), and (e) are two-dimensional radar images obtained by analyzing the radar signals, those images representing the locations directly above, directly below, at the right side, and at the left side with respect to the forward movement direction of the pipe line internal self-propelled vehicle, and (f) shows a convergence image obtained by analyzing the laser gyro signals and laser sensor signals.
Figure 7:
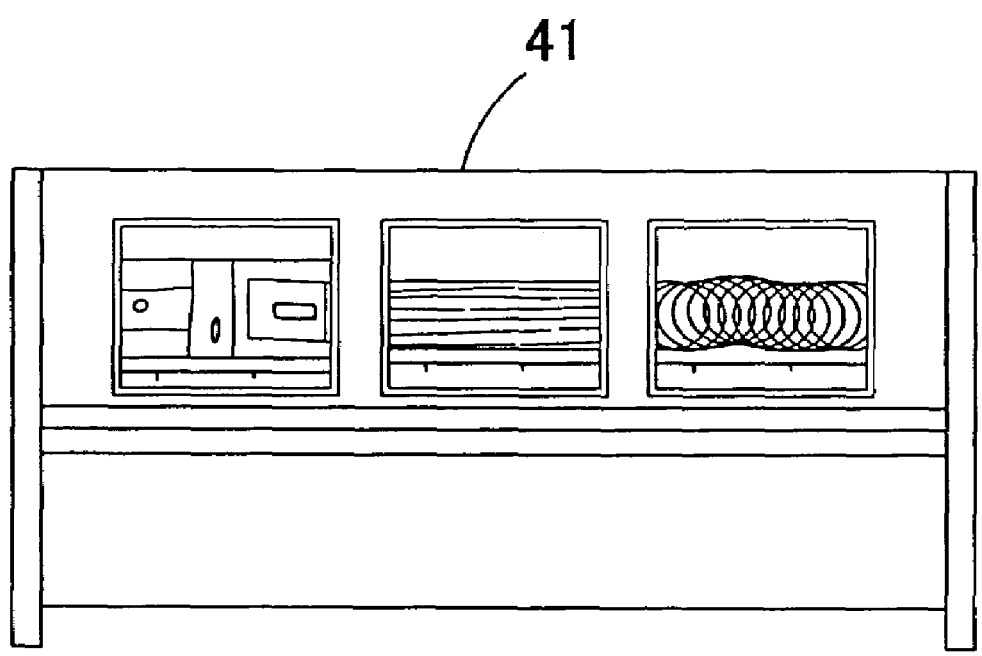
FIG. 7 is an explanatory drawing illustrating a display example on the display of the on-ground control unit of the first embodiment.

The control unit 2 receives and analyzes the signals outputted from the rotating radar antenna 11, forms a two-dimensional radar image with a traveling direction of the pipe line internal self-propelled vehicle, that is, the distance in the axial direction of the underground pipe as an abscissa and the distance in outward of the inner peripheral surface of the underground pipe line as an ordinate, and outputs this image to the printer. In the first embodiment, a two-dimensional radar image is formed outward of the inner peripheral surface in four locations: directly above, directly below, at the right side, and at the left side toward the advance direction of the pipe line internal self-propelled vehicle 1. Examples of respective printer outputs are shown in FIGS. 6(*b*) to (*e*). In those examples, 4-meter images are shown with a 1-meter pitch from the inspection initiation point measured by the infrared encoder 18. Further, those images can be also real-time displayed on a display of the control unit 2 as shown in FIG. 7. Search for cavities can be conducted by visually observing those images.

The camera using the fisheye lens 15, which is provided at the pipe line internal self-propelled vehicle 1 will be described below. The CCD camera equipped with the fisheye lens 15, which is mounted in the head part of the cylindrical body casing 20 is provided inside the body casing 20. An illumination lamp mounting portion 21 for the camera in the form of an octagonal truncated pyramid is mounted around the fisheye lens, and illumination lamps 16 for the fisheye lens camera are embedded in the tilted surfaces of the octagonal truncated pyramid. The inner peripheral surface of the underground pipe 9 is illuminated with the illumination lamp 16 for the fisheye lens camera, while the pipe line internal self-propelled vehicle 1 moves inside the underground pipe line 5, and images of the inner peripheral surface are picked up with the fisheye lens camera. The resultant signal is transmitted to the on-ground control unit 2 via the connector 35 for a connecting cable. The image picked up by the CCD camera via the fisheye lens is the image of a circle of a greatly reduced size. This image is converted into an expanded image by the on-ground control unit and outputted to the printer. The expanded image as referred to herein is a detailed plane image for which the distance in the traveling direction of the pipe line internal self-propelled vehicle, that is, the distance in the axial direction of the underground pipe, is selected as an abscissa, and the inner periphery of the underground pipe line is selected as an ordinate. An example of such an image outputted to the printer is shown in FIG. 6(*a*). Furthermore, those images can be also real-time displayed on a display of the on-ground control unit 2, as shown in FIG. 7. This image is the image of the inner peripheral surface of the underground pipe 9, and cracks or fractures in the underground pipe can be detected by visually observing those images.

A laser gyro (not shown in the figures), which is provided in the pipe line internal self-propelled vehicle 1 for measuring the inclination of the pipe line internal self-propelled vehicle 1 with the object of measuring the inclination of the axial direction of the underground pipe line 5 with respect to the horizontal direction and the laser sensor 17 for measuring the internal space variations of the underground pipe 9 will be described hereinbelow. The laser gyro is a gyro using a laser. It is provided inside the body casing 20 and can detect the inclination of the traveling direction of the pipe line internal self-propelled vehicle 1. Because the inclination of the traveling direction of the pipe line internal self-propelled vehicle 1 is caused by the inclination of the axial direction of the underground pipe line 5, the laser gyro can detect the inclination of the axial direction of the underground pipe line 5. Furthermore, the laser sensor 17 is provided in the rear end of the cylindrical body casing 20 and is composed of a laser generator, which rotates around the body casing 20 along a ring-like guide mounted on the surface of the body casing 20, and an optical receiver for picking up the light of the generating laser that was reflected from the inner peripheral surface of the underground pipe 9. The signals of those laser gyro and laser sensor 17 are transmitted to the on-ground control unit 2 via the connector 35 for ca connecting cable, analyzed in the control unit 2, and outputted to the printer as a three-dimensional convergence image. Here, the convergence refers to the shape of the inner periphery of the underground pipe, and the three-dimensional convergence image is an image obtained by selecting an X axis as the traveling direction of the pipe line internal self-propelled vehicle, that is, the distance in the axial direction of the underground pipe, an Y axis as the horizontal direction of a circle formed by inner periphery of the underground pipe, and Z axis as the vertical direction to this circle, plotting the X axis, Y axis, and Z axis on a plane, and plotting on the same plane the shape of the inner periphery of the underground pipe intermittently along the axial direction of the underground pipe, while reflecting the inclination of the underground pipe line obtained from the analysis of the laser gyro signals. An example of such an image outputted to the printer is shown in FIG. 6(*f*). Furthermore, those images can be also real-time displayed on a display of the control unit 2 as shown in FIG. 7. This image, as described hereinabove, shows the shape of the inner periphery of the underground pipe 9. It can represent the pattern of cracks or irregularities on the inner peripheral surface of the pipe line, and visual observations of this image can detect cracks or fractures in the underground pipe.

The above-described radar image, expanded image, and convergence image are real-time displayed on a display of the control unit 2 and outputted to the printer, as described hereinabove. In this case, at the point in time the initial signals of those images are inputted in the control unit 2, an identification signal indicating that those signals represent data relating to the same observation ground point are assigned thereto and the signal together with the images are outputted to the printer or the images are simultaneously displayed on each display of the control unit 2 synchronously with the signal. The identification signal can be also represented by using the traveling distance of the pipe line internal self-propelled vehicle 1 from the inspection initiation point, which is obtained from the infrared encoder 18. Numerical values shown below each image in FIG. 6 are those identification signals and represent the distance from the inspection initiation point.

Thus establishing the correspondence between the radar images of the same observation point, expanded image, and convergence image makes it possible to establish the correspondence between the position of a specific image on the expanded image or the convergence image and the position where a cavity is present in the radar image, thereby making it possible to determine reliably the position where the cavity is present. Alternatively, establishing the correspondence between the expanded image and the convergence image makes it possible to determine reliably the position where a deformation, crack, or fracture is present inside the underground pipe.

Figure 8:
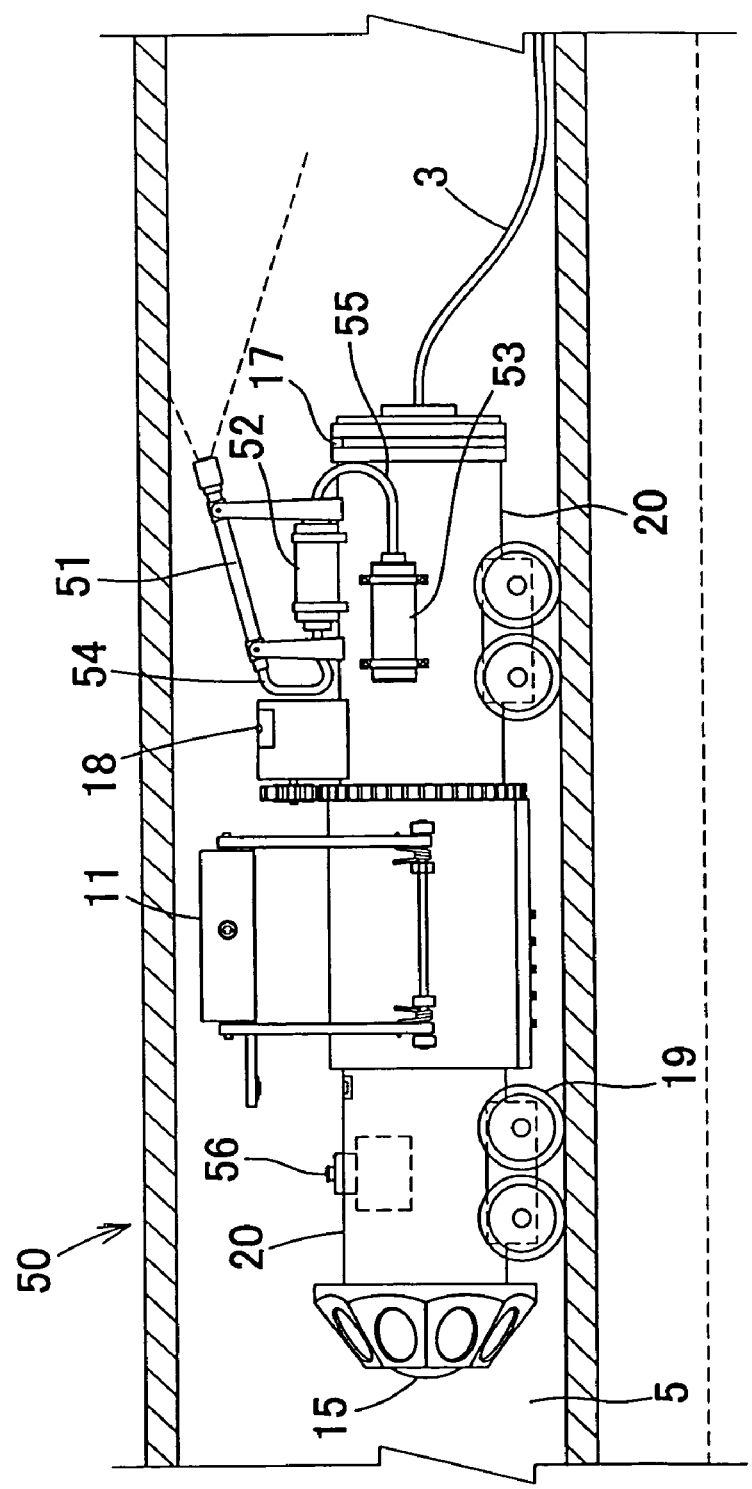
FIG. 8 is a side view of the pipe line internal self-propelled vehicle of the second embodiment.

The underground pipe line internal inspection device of the second embodiment will be described below. The underground pipe line internal inspection device of the second embodiment has a function of inspecting concrete underground pipe lines. In this device, the pipe line internal self-propelled vehicle of the underground pipe line internal inspection device of the first embodiment additionally comprises spraying means for spraying a concrete deterioration diagnostic reagent over the inner peripheral surface of the concrete of the underground pipe line. FIG. 8 is a side surface view of a pipe, line internal self-propelled vehicle 50. Referring to FIG. 8, a spraying nozzle 51, an electric pump 52, and a reagent container 53 are installed at the body casing 20, and the spraying means is constituted by linking them with a nozzle-pump linking hose 54 and a pump-container linking hose 55. The reference numeral 56 stands for a toxic gas detection sensor.

Inside concrete underground pipes used for sewage lines and the like, hydrogen sulfide present in sewage is converted into sulfuric acid by sulfur-oxidizing bacteria, and the sulfuric acid reacts with cement components present in the concrete and produces an expandable mineral called ettringite. The ettringite further reacts with sulfuric acid and is converted into gypsum dehydrate. As a result, the concrete is embrittled and corrosion thereof is enhanced. Accordingly, a concrete deterioration diagnostic reagent for judging the presence of concrete deterioration induced by sulfuric acid has been developed for judging the presence of concrete deterioration caused by sulfuric acid. This reagent reacts with sulfuric acid, and if it is sprayed over the concrete surface, then the surface to which the reagent has adhered changes color depending on whether the sulfuric acid, that is, deterioration of concrete, is present or not. For example, with a reagent obtained by adding a cellulose ether-based stabilizing agent to a mixture of sodium triphenylrozaniline sulfonate and P-benzenesulfonic acid azoresorcinol, the surface of the sprayed concrete is colored reddish brown if the surface is sound or white is the surface is corroded. Therefore it is possible to judge as to whether the concrete is corroded or not by checking the color of the surface of the inner peripheral surface of the concrete of the underground pipe after the reagent has been sprayed thereon.

The presence of concrete corrosion in the concrete underground pipes such as sewage pipes is detected by using the above-described reagent and the pipe line internal self-propelled vehicle 50 of the second embodiment. Thus, after the reagent container 53 of the pipe line internal self-propelled vehicle 50 of the second embodiment has been filled with the aforementioned reagent, the pipe line internal self-propelled vehicle 50 is moved forward in the underground pipe channel 5. During this forward movement, the reagent present in the reagent container 53 is supplied by the electric pump 52 to the spraying nozzle 51 via the pump-container linking hose 55 and nozzle-pump linking hose 54 and is sprayed from the nozzle onto the inner peripheral surface of the concrete of the underground pipe line 5 behind the pipe line internal self-propelled vehicle 50 with respect to the traveling direction thereof. Then, the pipe line internal self-propelled vehicle 50 is moved backward and the inner peripheral surface of the underground pipe line 5 onto which the reagent has already been sprayed and which has assumed a color that varies depending on the presence of concrete deterioration is photographed with the fisheye lens camera, which is disposed behind the fisheye lens 15 of the pipe line internal self-propelled vehicle 50, during this backward movement. Based on the images thus picked up, the on-ground control unit of the second embodiment forms an expanded image, the presence or absence of deterioration on the inner peripheral surface of the concrete is judged upon from the expanded image, and the results are displayed in a real time mode.

No conversion of hydrogen sulfide into sulfuric acid by sulfur-oxidizing bacteria occurs on the concrete surface that is constantly immersed in water. Therefore, the above-described inspection is unnecessary. In this case, the reagent spraying area is limited to the zone outside the area where the concrete is constantly immersed in water.

The pipe line internal self-propelled vehicle 50 of the second embodiment carries a toxic gas detection sensor 54. The presence of toxic gases such as hydrogen sulfide is inspected together with making a decision relating to the deterioration of the inner peripheral surface of the concrete in the above-described manner, and the results are displayed by the on-ground control unit of the second embodiment.

With the above-described underground pipe line internal inspection device of the second embodiment, a concrete deterioration diagnostic reagent which changes the color of the surface to which it has adhered according to the presence or absence of concrete deterioration is sprayed on the inner peripheral surface of concrete in the underground pipe line and the results are picked up with a fisheye lens camera. Therefore, a decision relating to the presence or absence of concrete deterioration in the line can be made based on the picked-up images.

Further, the above-described underground pipe line internal inspection device of the second embodiment, similarly to the underground pipe line internal inspection device of the first embodiment, has a radar for cavity inspection, a gyro, a laser sensor, and a function of establishing the correspondence between the radar image and the expanded image, or an infrared encoder. Therefore, it demonstrates functions and effects identical to those explained with reference to the underground pipe line internal inspection device of the first embodiment.

Figure 9:
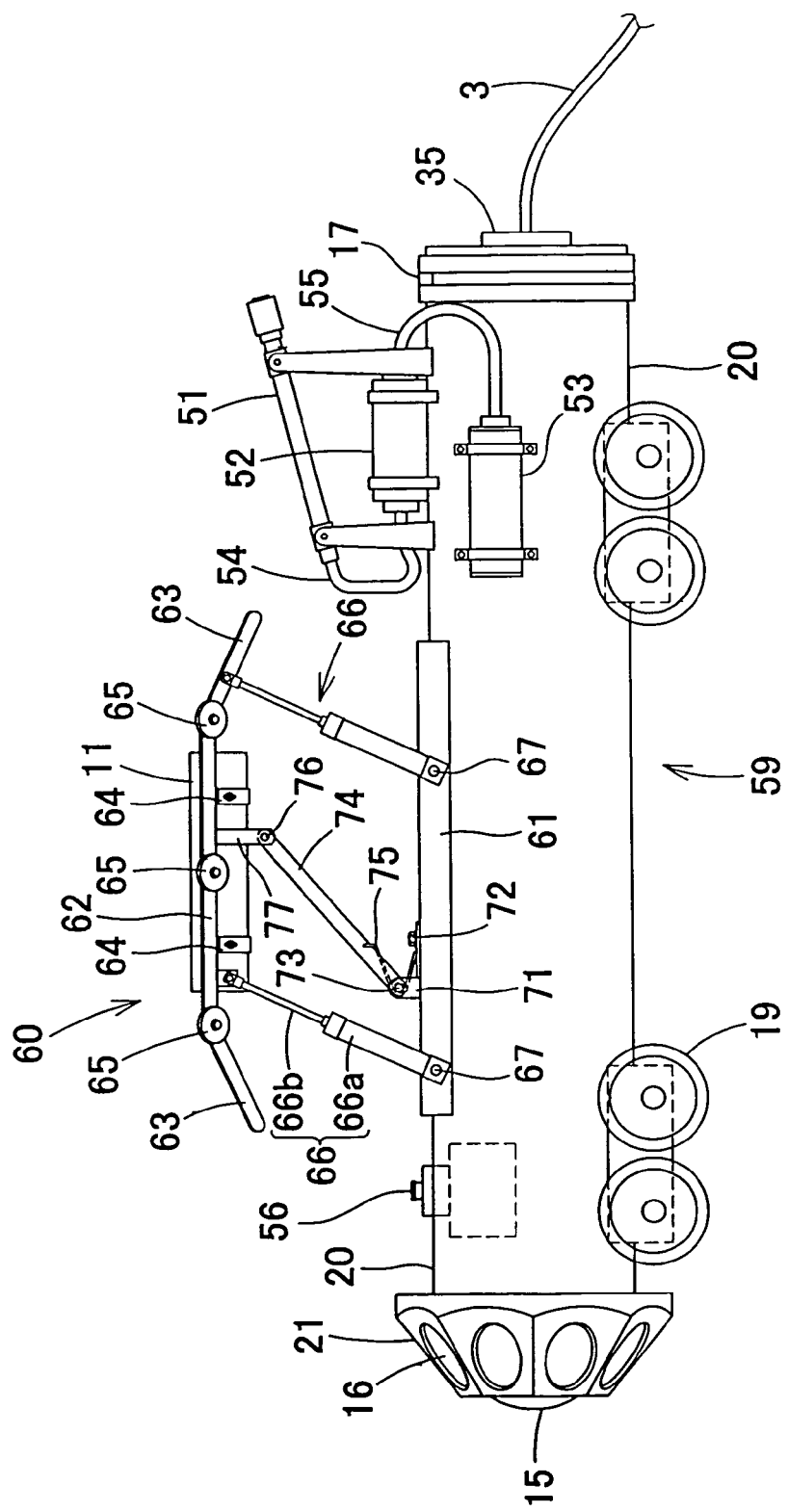
FIG. 9 is a side view of the pipe line internal self-propelled vehicle of the third embodiment.
Figure 10:
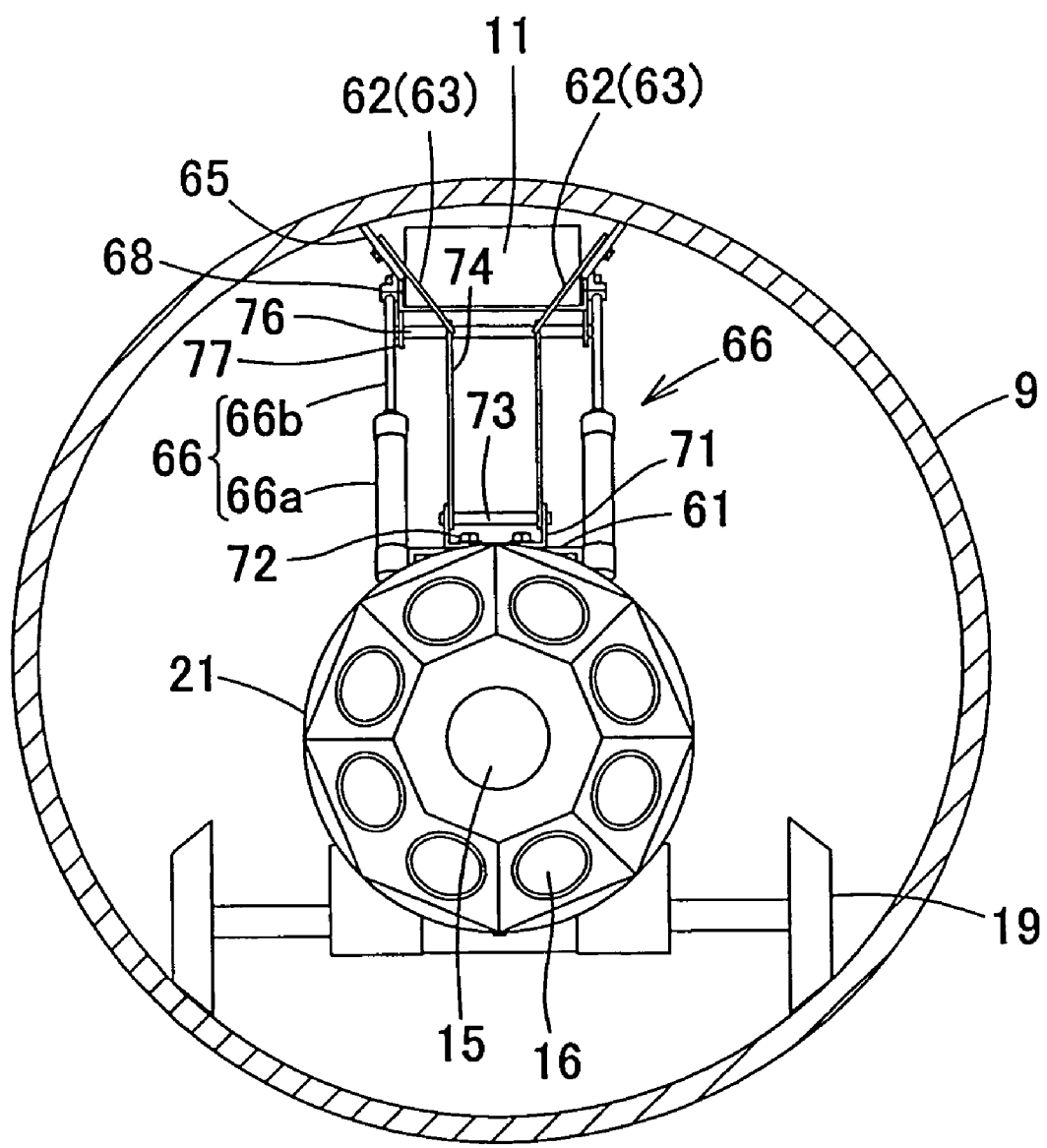
FIG. 10 is a plan view illustrating the insertion of the pipe line internal self-propelled vehicle of the third embodiment into the underground pipe.
Figure 11:
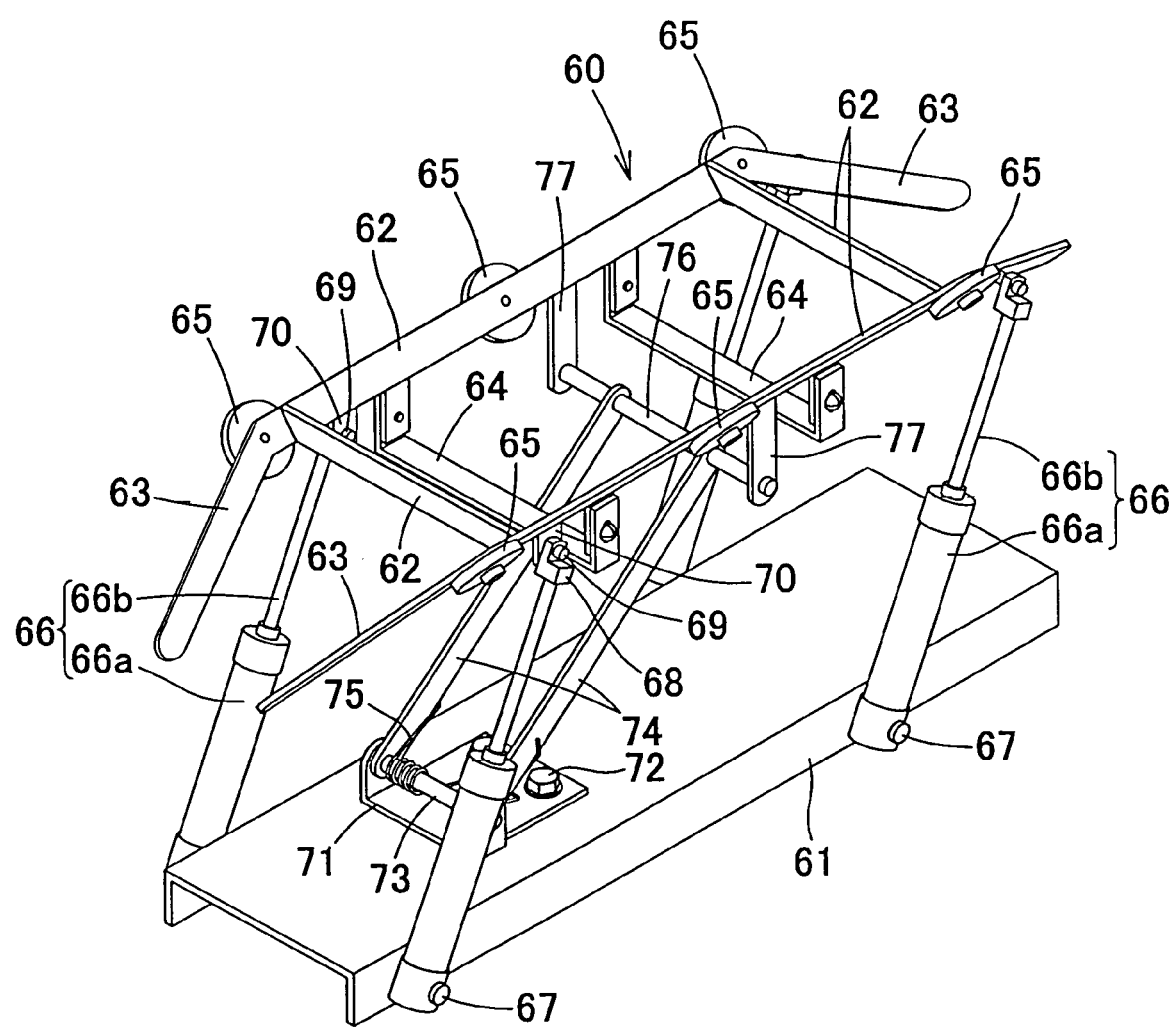
FIG. 11 is a perspective view of the parallel link mechanism for lifting and lowering the antenna in the pipe line internal self-propelled vehicle of the third embodiment.
Figure 12:
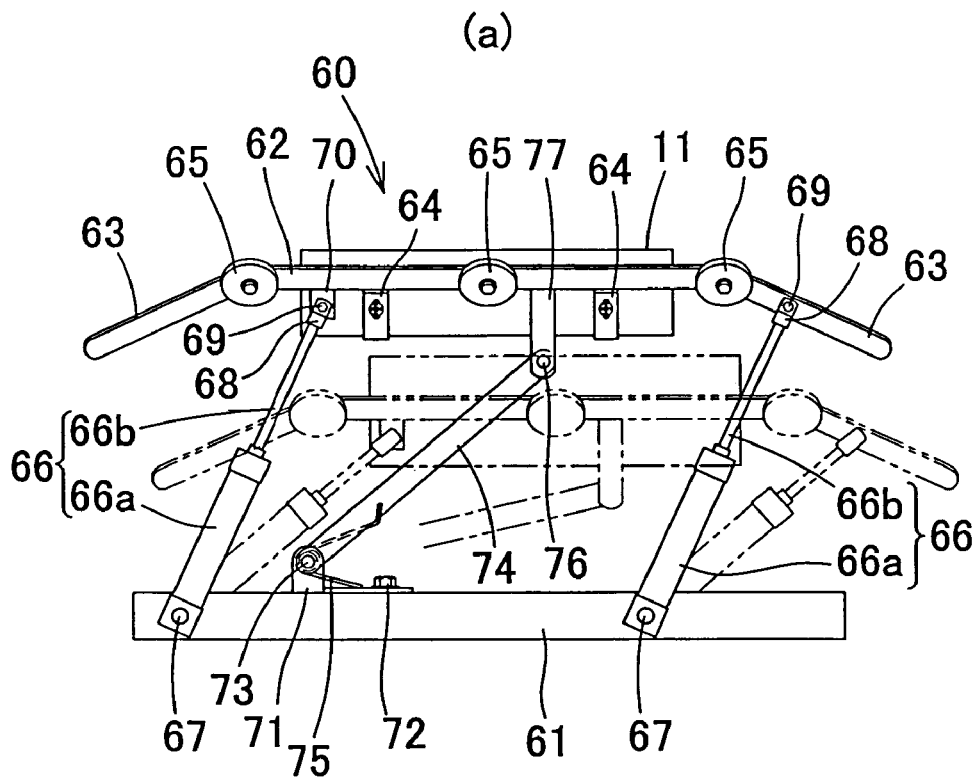
FIG. 12 is an explanatory drawing illustrating the operation state of the parallel link mechanism for lifting and lowering the antenna of the third embodiment; (a) shows the usual state and (b) shows a state in which the upper surface of the antenna is inclined in the front-rear direction to follow the shape of the ceiling inside the pipe line of the underground pipe.
Figure 12:
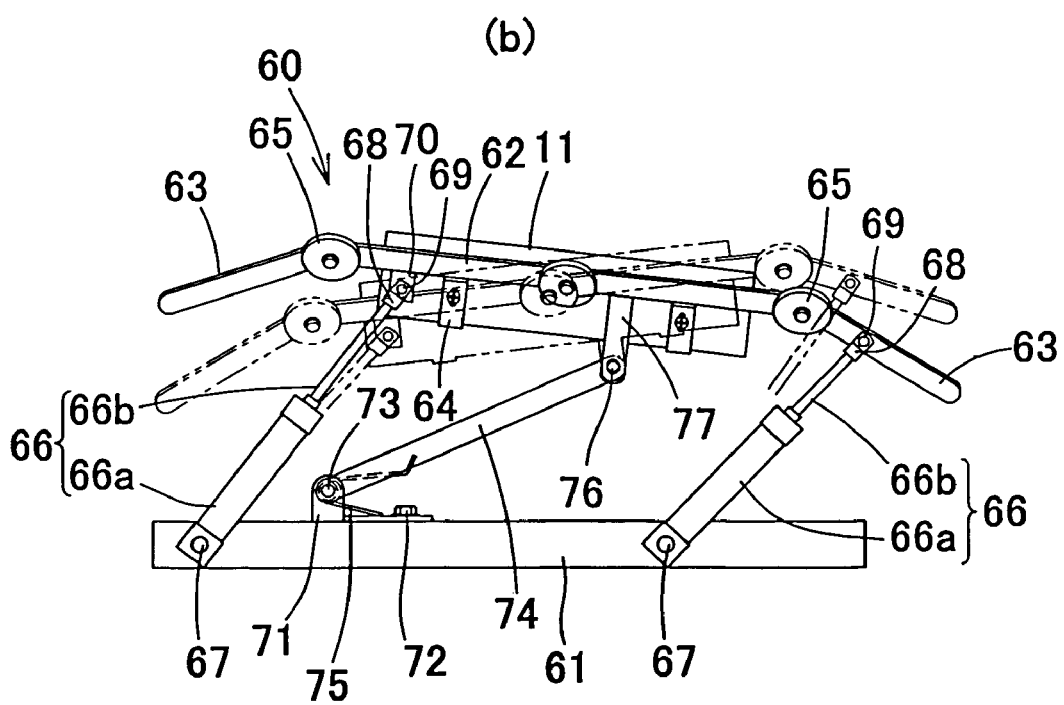

In the above-described underground pipe line internal inspection device of the first embodiment and second embodiment, the radar antenna was rotated along the inner peripheral surface inside the pipe line of an underground pipe in order to inspect cavities present in the ground around the underground pipe. However, there are cases where only the inside of the ground above the ceiling inside the pipe line is the object of cavity inspection. The underground pipe line internal inspection device of the third embodiment that is used in such a case will be described below. In the underground pipe line internal inspection device of the third embodiment, a parallel link mechanism for raising and lowering the antenna, which holds the radar antenna, is provided at the pipe line internal self-propelled vehicle instead of the mechanism for rotating the radar antennal along the inner peripheral surface inside the pipe line of the underground pipe in the underground pipe line internal inspection device of the second embodiment. All other components are absolutely identical to those of the underground pipe line internal inspection device of the second embodiment. Therefore, the parallel link mechanism for raising and lowering the antenna will be mainly described below. FIG. 9 is a side view of the pipe line internal self-propelled vehicle of the device for inspecting the inside of an underground pipe line of the third embodiment. FIG. 10 is a front view relating to a case in which the pipe line internal self-propelled vehicle was inserted into the underground pipe. FIG. 11 is a perspective view of the parallel link mechanism for raising and lowering the antenna. FIG. 12 is an explanatory figure illustrating the operation state of the parallel link mechanism for raising and lowering the antenna. In FIGS. 9 to 12, components identical to those of the pipe line internal self-propelled vehicle of the device for inspecting the inside of an underground pipe line of the second embodiment are assigned with the same symbols.

In FIGS. 9 to 12, the parallel link mechanism 60 for raising and lowering the antenna in the pipe line internal self-propelled vehicle 59 of the device for inspecting the inside of an underground pipe line of the third embodiment has the following structure.

A rectangular antenna support frame 62 is so disposed that the short side thereof is aligned in the front-back direction along the traveling direction of the pipe line internal self-propelled vehicle 59 and comprises four guide bars 63 extended with downward inclination forward or backward at the front end or rear end of the long side of the antenna support frame 62. The inner side surfaces of the long sides of the antenna support frame 62 and guide bars 63 are inclined so as to open with upward and outward inclination with respect to the traveling direction of the pipe line internal self-propelled vehicle 59. Further, guide rollers 65 are rotatably mounted on the outer side surfaces of the long sides of the antenna support frame 62 and guide bars 63 so that the rollers somewhat protrude with upward and outward inclination along the inclination plane of the antenna support frame 62. The radar antenna 11 is in the form of rectangular parallelepiped and the surface thereof that emits electromagnetic waves faces upward. The antenna is held by the antenna support frame 62 and two U-like antenna support members 64 that are suspended and provided so as to hang across from both long sides of the antenna support frame 62.

The radar antenna 11 held by the antenna support members 64 is supported by four dampers installed almost parallel each other so that the total length thereof can be changed by extension or contraction. Thus, a mounting base 61 with a U-like cross section crossing the longitudinal direction is mounted by welding on the upper surface of the body casing 20 so that the recessed surface thereof faces down and the longitudinal direction thereof assumes the same direction as the axial direction of the body casing 20 of the pipe line internal self-propelled vehicle 59. The end portions of damper cylinders 66a of the four dampers 66, which are composed of damper cylinders 66a and damper rods 66b thereof and installed almost parallel each other so that the total length thereof can be changed by extension or contraction, are rotatably pivotally attached with the pivot pins 67 in two, front and rear, places on both side pieces of the mounting base 61, so that the distal ends of the damper rods 66b are directed upward with rearward inclination. The distal ends of damper rods 66b of the two dampers 66 (of the four dampers 66) that are mounted on the front end portions of the side pieces of the mounting base 61 are rotatably pivotally attached by using crevices 69 to crevice pin linkages 70 provided vertically downwardly from the front end portions of the long sides of the antenna support frame 62, via the crevices 68 attached in a bottle cap fashion to the distal end thereof. The distal ends of the damper rods 66b of the two dampers 66 mounted on the rear portions of the side pieces of the amounting base 61 are rotatably pivotally attached by using crevice pins 69 to the guide bars 63 provided in the extending condition from the rear ends of the long sides of the antenna support frame 62 via the crevices 68 attached in a bottle cap fashion to the distal end thereof.

Further, from the centers of both long sides of the antenna support frame 62, the two connection pin linkages 77 are provided in vertical conditions so that the lower ends thereof are located below the lower end of the antenna support member 64, the lower end portions of the connection pin linkages 77 are connected by the connection pins 76, and one end of each of the two link bars 74 is rotatably fitted in a position obtained by dividing the entire length of the connection pins 76 by three, so that the two link bars are parallel to each other and the other ends thereof are inclined forward and downward. Thus, the other end of the link bar 74 is rotatably fitted on a support pin 73 connecting both side pieces provided vertically upward parallel to the axial direction of the main casing 20 of the pipe line internal self-propelled vehicle 59 and serving as side pieces of the bracket 71 fixed with the bracket fixing bolts on the upper surface close to the front portion of the mounting base. One end of the link bar 74 is impelled by an impelling spring 75 covering the support pin 73, so as to lift the link bar 74 upward. Under the effect of this impelling action, the antenna support frame 62 is pushed toward the ceiling inside the pipe line of the underground pipe 9 when the pipe line internal self-propelled vehicle 59 travels inside the pipe line of the underground pipe 9 and the guide roller is brought into contact with the ceiling surface, thereby bringing the radar antenna 11 as close as possible to the ceiling surface.

FIG. 12 is an explanatory drawing illustrating the operation state of the parallel link mechanism 60 for lifting and lowering the antenna, which has the above-described structure. FIG. 12(a) illustrates the usual operation state and FIG. 12(b) illustrates the state in which the front surface of the radar antenna 11 is inclined in the front-back direction so as to follow the shape of the ceiling inside the pipe line of the underground pipe 9. Thus, when the ceiling inside the pipe line of the underground pipe 9 is flat and has no protrusion or adhered matter, as shown in FIG. 12(a), the antenna support frame 62 moves in a parallel mode and adjusts the height of the radar antenna 11 to match the height of the ceiling. However, when protrusions or adhered matter is present on the ceiling inside the pipe line of the underground pipe 9, as shown in FIG. 12(b), the four dampers 66 supporting the antenna support frame 62 are extended or contracted appropriately, thereby following the shape of the ceiling and inclining the upper surface of the radar antenna 11, that is, the entire frame of the antenna support frame 62, in the front-rear direction.

With the apparatus for inspecting the inside of an underground pipe line of the above-described third embodiment, by contrast with the configuration in which the antenna is caused to rotate along the inner peripheral surface inside the pipe line of the underground pipe, it is not necessary to use a motor for rotating the antenna, the mechanical structure can be simplified, the upper surface of the antenna can follow the shape of the ceiling, and the accuracy of inspection can be increased.

Figure 13:
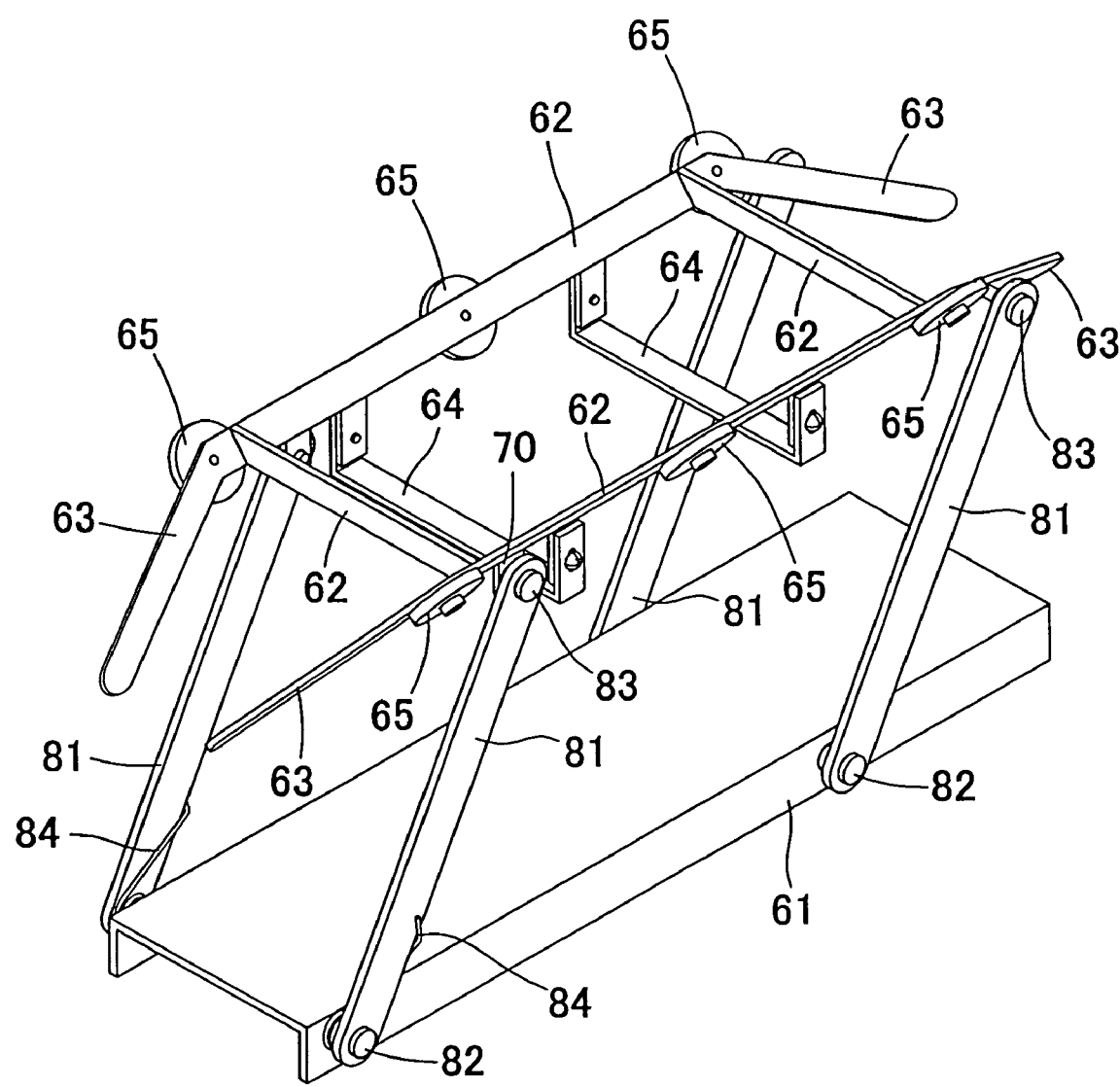
FIG. 13 is a perspective view illustrating another example of the parallel link mechanism for lifting and lowering the antenna of the third embodiment.

In the above-described third embodiment, the upper surface of the radar antenna 11 is inclined in the front-rear direction according to the shape of the ceiling. However, because the mechanism becomes complex, the parallel link mechanism for lifting and lowering the antenna may be provided only with the function of implementing parallel movement of the antenna support frame 62 and adjusting the height of the radar antenna 11. FIG. 13 shows an example of the parallel link mechanism for lifting and lowering the antenna in this case. The aforementioned link bar 74 and components associated therewith are removed and four link bars 81 of the same length are used instead of the damper 66. Among them, the front two link bars 81 are rotatably pivotally attached at one end thereof by using upper pivot pins 83 to a crevice pin linkage 70 provided in a vertical condition downward from the front end portion at the long side of the antenna support frame 62, and rotatably pivotally attached at the other end thereof by using lower pivot pins 82 to the front end portion of the side piece of the mounting base 61. The impelling springs 84 are so provided as to cover the lower pivot pins 82 and impel the two link bars 81 so as to lift one end thereof upward. The two rear link bars 81 are rotatably pivotally attached at one end thereof by using upper pivot pins 83 to the guide bar 63, and are rotatably pivotally attached at the other end thereof by using the lower pivot pins 82 to the rear portion of the side piece of the mounting base. With such a parallel link mechanism for lifting and lowering the antenna, the mechanism can be further simplified.

Figure 14:
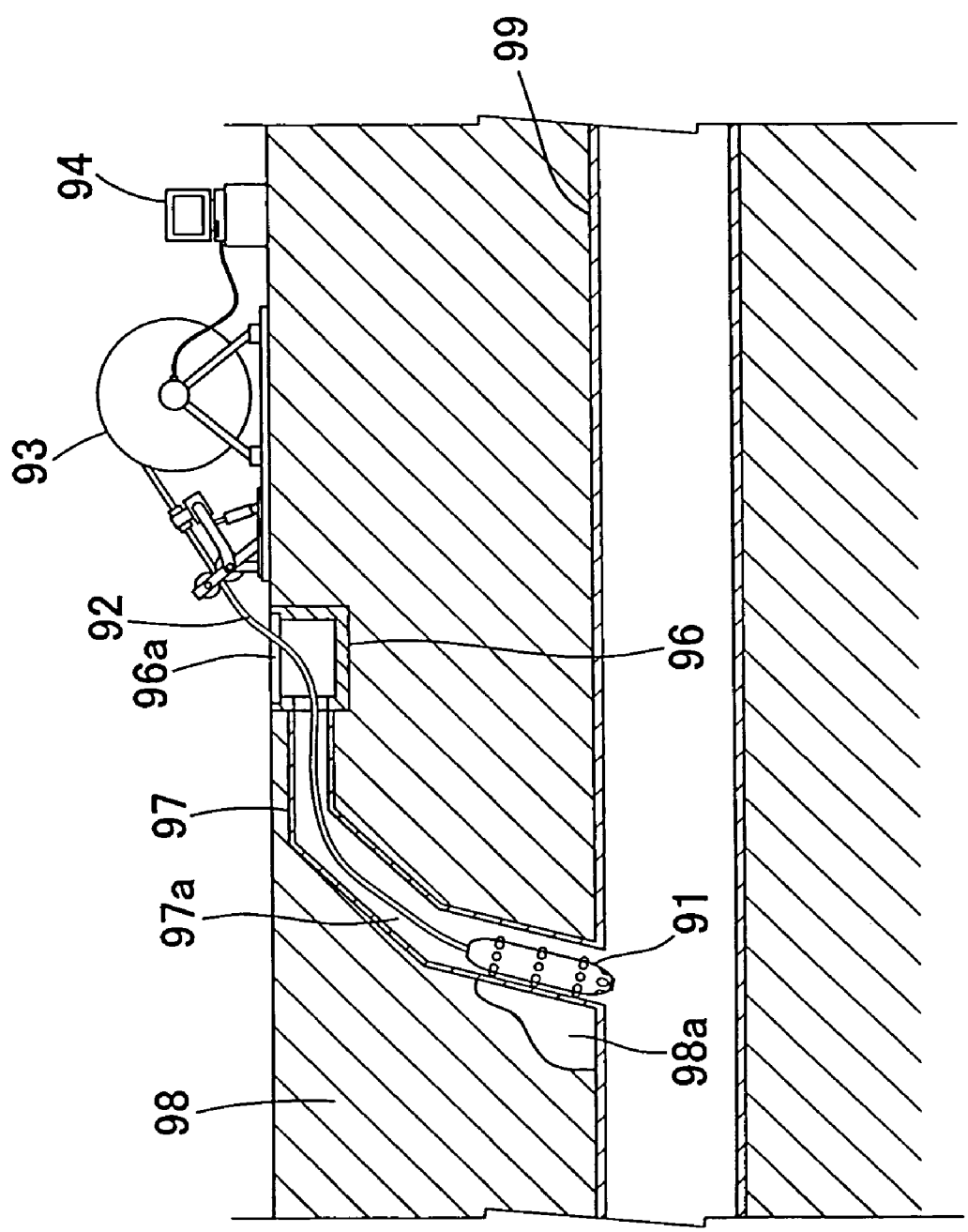
FIG. 14 illustrates the usage state of the device for inspecting the inside of an underground pipe line of the fourth embodiment.

The apparatus for inspecting the inside of an underground pipe line of the fourth embodiment will be described below. The apparatus for inspecting the inside of an underground pipe line of the fourth embodiment is an inspection apparatus used for inspecting the lateral sewers of small diameter that are connected to the main sewer pipe. FIG. 14 illustrates the usage stage of the apparatus for inspecting the inside of an underground pipe line of the fourth embodiment. In FIG. 14, the apparatus for inspecting the inside of an underground pipe line comprises an inspection unit 91, a cable 92, a cable winding unit 93, and an on-ground control unit 94 as the main structural components. The inspection unit is designed for conducting inspection inside a pipe line 97a of an lateral sewer 97 or inside the surrounding ground. The on-ground control unit 94 serves to process the signals outputted from the inspection unit 91. The cable 92 connects the inspection unit 91 and the on-ground control unit 94. Further, the cable winding unit 93, in addition to winding up the cable 92, also controls the location and posture of the inspection unit 91 in the pipe line 97a of the lateral sewer 97. In FIG. 14, the reference symbol 96 stands for a attachment box, 96a—a box lid, 97—an lateral sewer, 97a—a pipe line of the lateral sewer, 98—ground, 98a—a cavity in the ground, and 99—a main sewer pipe.

Figure 15:
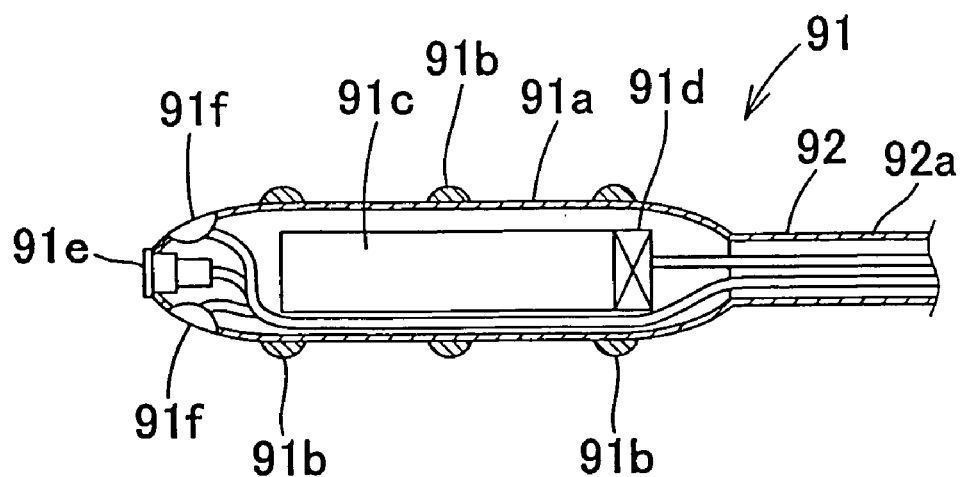
FIG. 15 is a cross-sectional view of the inspection unit of the device for inspecting the inside of an underground pipe line of the fourth embodiment.
Figure 16:
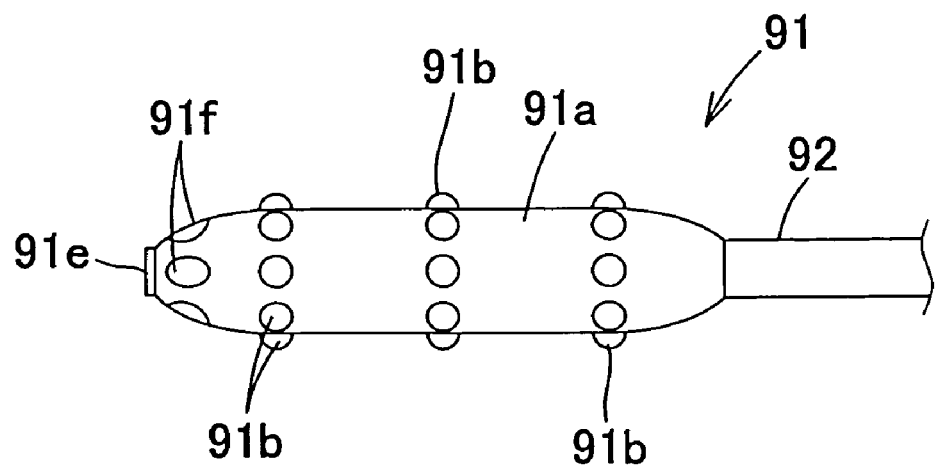
FIG. 16 illustrates the external appearance of the inspection unit of the device for inspecting the inside of an underground pipe line of the fourth embodiment.

FIG. 15 is a cross-sectional view of the inspection unit 91. FIG. 16 illustrates external appearance of the inspection unit 91. The inspection unit 91 has a cylindrical body 91a which is inserted and used inside the pipe line 97a of the lateral sewer 97. Supporters 91b in the form of semispherical protrusions are provided on the surface of the body 91a. They are provided to ensure smooth contact between the inner peripheral surface of the lateral sewer 97 and the inspection unit 91 when the inspection unit 91 moves forward or backward or when it is rotated about its axis. Further, as shown in FIG. 15 and FIG. 16, a radar 91c, a gyro 91d, a fisheye lens camera 91e, and an illumination 91f are provided in the inspection unit 91.

The radar 91c is provided with an antenna, but it has a configuration such that electromagnetic waves are emitted from the antenna unidirectionally from the outer peripheral surface of the body 91 along the inner peripheral surface of the lateral sewer 97 in order to reduce the size of the inspection unit and has a function of inspecting the cavities 98a present inside the ground 98 surrounding the lateral sewer 97. Therefore in order to conduct the inspection of the ground surrounding the lateral sewer 97 over the entire periphery thereof, the radar 91c, that is, the body 91a of the inspection unit 91, has to be rotated inside the pipe line 97a of the lateral sewer 97 around the axis thereof. The gyro 91d has a function of measuring the direction of the rotation axis and the rotation angle. The fisheye lens camera 91e has a function of picking up the image of the inner peripheral surface forward in the insertion direction of the inspection unit 91 inside the pipe line 97a of the lateral sewer 97. The illumination 91f is used for image pick up by the fish eye camera 91e. Further, in the rear portion of the body 91a of the inspection unit 91, the cable 92 is connected coaxially with the body 91a. The cable 92 is covered with a flexible tubing 92a having flexibility. If the cable 92 is pushed or pulled, the body 91a of the inspection unit 91 can be moved forward or backward, and if the cable 92 is rotated, the body 91a of the inspection unit 91 can be rotated about the axis thereof as a center.

Figure 17:
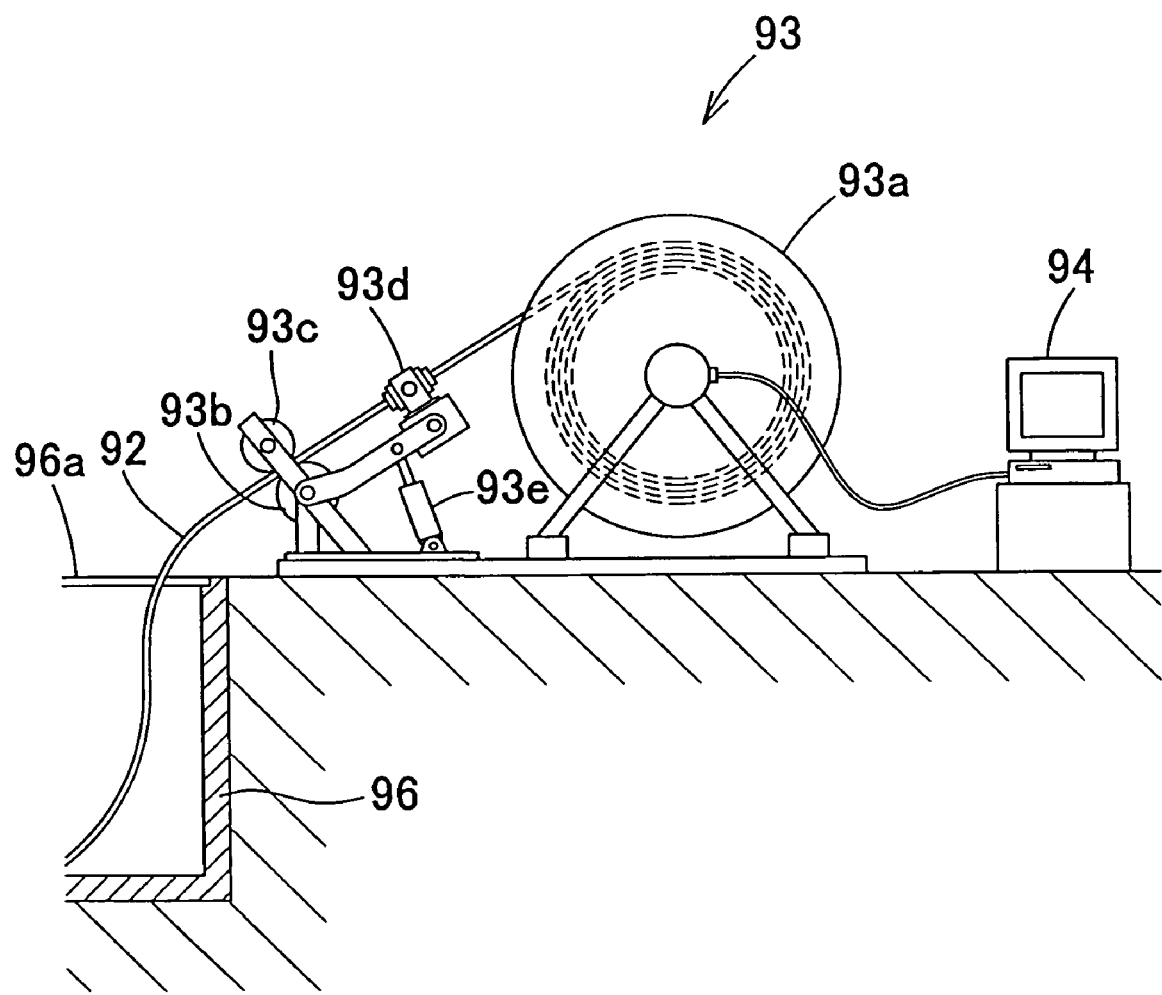
FIG. 17 illustrates the external appearance of the cable winding unit of the device for inspecting the inside of an underground pipe line of the fourth embodiment.

FIG. 17 illustrates the external appearance of the cable winding unit 93. The cable winding unit 93, as shown in FIG. 17, comprises a cable winding drum 93a, a cable draw-out roller 93b, an encoder 93c, a cable rotation mechanism 93d, and a height adjustment mechanism 93e. The cable winding drum 93a has a function of winding up the cable 92. The winding drum can be rotated forward and reverse by a motor drive. The cable draw-out roller 93b has a function of drawing the cable 92 out or winding it back with a motor drive in order to advance the body 91a of the inspection unit 91 forward or rearward inside the pipe line 97a of the lateral sewer 97. The encoder 93c has a function of measuring the draw-out length of the cable 92. The output signal of the encoder 93c is inputted into the on-ground control unit 94. The cable rotation mechanism 93d has a function of rotating the cable 92, strictly speaking, the flexible tube 92a covering the cable 92, with the object of rotating the body 91a of the inspection unit 91 inside the pipe line 97a of the inspection unit 91. Further, the height adjustment mechanism 93e has a function of adjusting the height of the cable 92 according to the length thereof wound on the cable winding drum 93a. A control box for controlling the cable winding drum 93a, cable draw-out roller 93b, and cable rotation mechanism 93d is provided in the cable winding unit 93 (this control box is not shown in the figure). The height adjustment mechanism 93e automatically adjusts the height of the cable according to the length of the cable 92 wound on the cable winding drum 93a. Further, an end of the cable 92 wound around the cable winding drum 93a is connected to the on-ground control unit 94. The on-ground control unit 94 is provided with a processing unit such as a microcomputer, a display, a printer, and the like. It has a function of receiving the signals from the radar 91c, gyro 91d, fisheye lens camera 91e, and encoder 93c, processing those signals, and displaying the inspection results on the display or printing them out.

A method for using the device for inspecting the inside of the underground pipe line of the fourth embodiment and operation thereof will be described below. Referring to FIG. 14, the inspection unit 91 is inserted from the attachment box 96 into the pipe line 97a of the lateral sewer 97 embedded into the ground 98. When the inspection unit is inserted, the inspection unit 91 can be positioned in the prescribed location inside the pipe line 97a of the lateral sewer 97 by actuating the cable winding drum 93a and cable draw-out roller 93b. In addition, the inspection unit 91 can be rotated inside the pipe line 97a of the lateral sewer 97 by actuating the cable rotation mechanism 93d.

Figure 18:
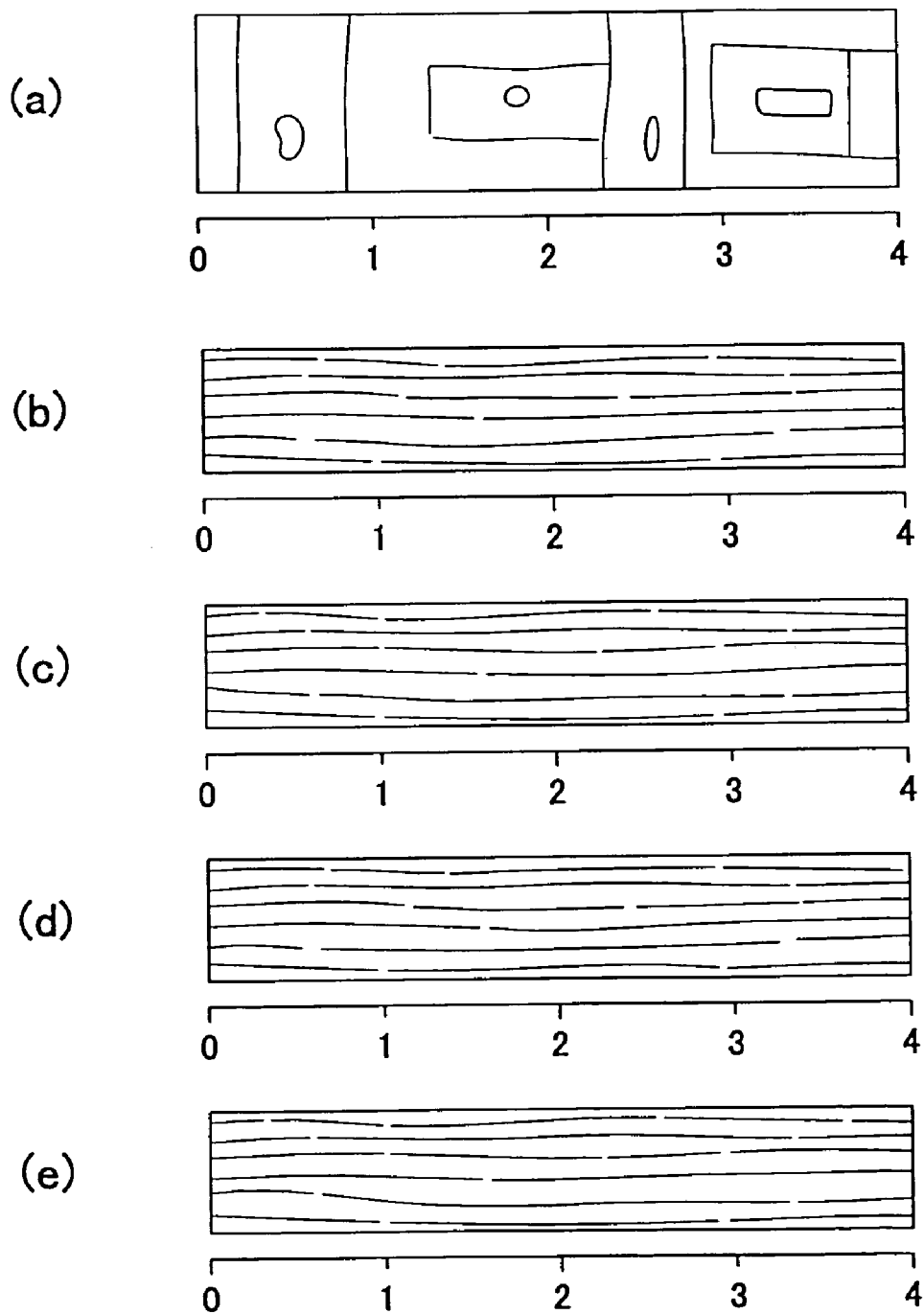
FIG. 18(a) shows an expanded image based on the images picked up by the fisheye lens camera in the device for inspecting the inside of an underground pipe line of the fourth embodiment, and (b), (c), (d), and (e) are two-dimensional radar images obtained by analyzing the radar signals, those images representing the locations directly above, directly below, at the right side, and at the left side with respect to the forward movement direction of the pipe line internal self-propelled vehicle.

As for the inspection technique, usually, the inspection unit 91 is initially inserted into the pipe line 97a of the lateral sewer 97, without actuating the cable rotation mechanism 93d, that is, without rotating the inspection unit 91 inside the pipe line 97a of the lateral sewer 97, the inside of the pipe line 97a is illuminated by illumination 91f as the inspection unit is advanced forward and the image of the inside of the pipe line 97a of the lateral sewer 97 is picked up with the fisheye lens camera 91e. The fisheye lens camera 91e comprises a CCD and the signal thereof is inputted into the on-ground control unit 94. The image of the CCD camera picked up via the fisheye lens is a round image which is greatly distorted. In the on-ground control unit 94, this image is converted into the expanded image and outputted to the display or printer. Here, the expanded image is a detailed plane image for which the abscissa is an advance direction of the inspection unit 91, that is, the distance along the axial direction of the lateral sewer 97, and the ordinate is the inner periphery of the lateral sewer 97. An example of this image outputted to the printer is shown in FIG. 18(a). Further, such images can be also displayed in a real time mode on the display of the on-ground control unit 94. This image is an image of the inner peripheral surface of the lateral sewer 97 and cracks or fractures present on the lateral sewer 97 can be detected by visually observing those images.

Then, a cavity 98a present inside the ground 98 surrounding the lateral sewer 97 is inspected with the radar 91c by retracting the inspection unit 91 and rotating it about the axis thereof. The output signal of the radar 91c is inputted into the on-ground control unit 94 and analyzed. The analysis results are represented as a two-dimensional radar image for which the abscissa is an advance direction of the inspection unit 91, that is, the distance along the axial direction of the lateral sewer 97, and the ordinate is the distance in the outward direction of the inner peripheral surface of the lateral sewer 97 and outputted to the display or printer. In the present embodiment, two-dimensional radar images outward of the inner peripheral surface are plotted in four locations: directly above, directly below, at the right side, and at the left side in the advancement direction of the inspection unit on the inner periphery of the lateral sewer 97. The respective examples of printer outputs are shown in FIGS. 18(b) to (e). In those examples, 4-meter images are shown with a 1-meter pitch from the inspection start point measured by the encoder 93. The measurements are conducted with the encoder 93. Further, those images can be also displayed in a real time mode on a display of the on-ground control unit 94. Search for cavities can be carried out by visually observing those images.

With the above-described device for inspecting the inside of underground pipe line of the fourth embodiment, the radar

91c installed in the inspection unit 91 is constructed so that electromagnetic waves are emitted from the antenna unidirectionally from the outer peripheral surface of the body 91a toward the inner peripheral surface of the lateral sewer 97. As a result, the size of the inspection unit 91 is reduced. Therefore, the device can be used for inspecting the underground pipes of small diameter such as lateral sewers connected to the underground main sewer pipe.

Further, the cable 92 is connected coaxially with the body 91a to the rear portion of the body 91a of the inspection unit 91. The cable 92 is covered with a flexible tube 92a having flexibility, and if the cable 92 is pushed or pulled, the body 91a of the inspection unit 91 can be moved forward or backward. Therefore, the inspection unit 91 can be easily moved inside the pipe line 97a of the lateral sewer 97.

Further, if the cable 92 is rotated, the body 91a of the inspection unit 91 can be rotated about the axis thereof. Therefore, the ground surrounding the lateral sewer 97 can be inspected along the entire periphery of the lateral sewer with the radar 91c provided in the inspection unit 91.

Further, supporters 91b in the form of semispherical protrusions are provided on the surface of the body 91a of the inspection unit 91 in order to provide for smooth contact between the inner peripheral surface of the lateral sewer 97 and the inspection unit 91 when the inspection unit 91 is moved forward or backward or rotated about its axis. Therefore, the inspection unit 91 can be easily moved forward or backward or rotated about its axis.

The inspection unit 91 is also provided with the gyro 91d and, in combination with the encoder 93c provided at the cable winding unit 93, can measure the draw-out length of the cable 92 and the direction and rotation angle of the rotary shaft of the inspection unit 91 and can accurately find the position and posture of the inspection unit 91 inside the pipe line 97a of the lateral sewer 97, thereby making it possible to increase the inspection accuracy.

Further, the cable winding unit 93 is provided with the cable winding drum 93a, cable draw-out roller 93b, encoder 93c, cable rotation mechanism 93d, and height adjustment mechanism 93e that are driven by respective motors, the operation of drawing out the cable 92 or rotating the cable 92 can be conducted automatically and the inspection unit 91 can be moved forward or backward or rotated accurately and in an easy manner.

With the above-described device for inspecting the inside of an underground pipe line of the fourth embodiment, the cable winding drum 93a and cable draw-out roller 93b that are driven by respective motors are actuated in order to insert the inspection unit 91 into the pipe line 97a of the lateral sewer 97 and move it forward and backward therein, but those operations may be also conducted manually without using the motors. Furthermore, the motor-driven cable rotation mechanism 93d is actuated in order to rotate the inspection unit 91, but this operation may be also conducted manually.

Figure 19:
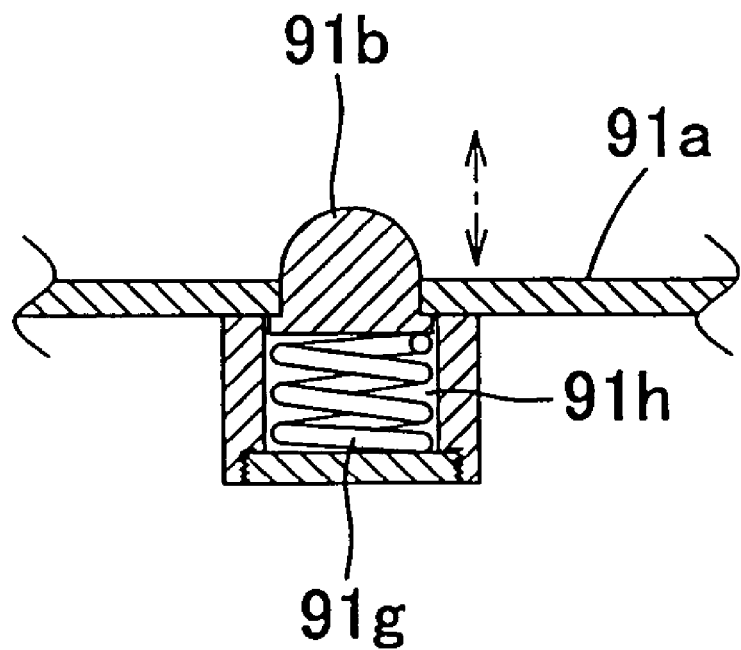
FIG. 19 is a cross-sectional view illustrating another example of a supporter of the inspection unit of the device for inspecting the inside of an underground pipe line of the fourth embodiment.

In the above-described device for inspecting the inside of an underground pipe line of the fourth embodiment, as shown in FIG. 19, the supporters 91b in the form of semispherical protrusions provided on the surface of the body 91a of the inspection unit 91 may be inserted, together with springs 91g abutting against the bottom portions thereof, into recesses 91h provided in the surface of the body 91a. As a result, the degree of protrusion of the supporters 91b from the outer peripheral surface of the lateral sewer 97 can be changed in the direction shown by an arrow in the figure according to changes in the inner diameter of the lateral sewer 97, thereby making it possible to bring the top portions of all the supporters 91b into contact with the inner peripheral surface of the lateral sewer 97 and to align the central axis of the body 91a of the inspection unit 91 with the central axis inside the pipe line 97a of the lateral sewer 97 even when the inner diameter of the lateral sewer 97 changes. Therefore, a constant distance can be maintained between the entire inner peripheral surface of the lateral sewer 97 and the radar 91c and uniform inspection with the radar 91c can be conducted over the entire inner peripheral surface of the lateral sewer 97.

Further, referring to FIG. 19, the antenna of the radar 91c can be always brought into closest contact with the inner peripheral surface of the lateral sewer 97, even if the inspection unit 91 is rotated, by using springs 91g with low elasticity for supporters 91b that are close to the antenna of the radar 91c, of all the supporters 91b provided at the surface of the body 91b of the inspection unit 91, and using springs 91g with high elasticity for the supporters 91b that are far from the antenna of the radar 91c. With such a configuration, the antenna of the radar 91c can be always brought into closest contact with the inner peripheral surface of the lateral sewer 97 even if the inner diameter of the lateral sewer 97 changes.

Further, in the cable rotation mechanism 93d provided in the cable winding unit 93 in the above-described device for inspecting the inside of an underground pipe line of the fourth embodiment, the cable winding drum 93a is in a fixed state, only the flexible tube 92a, which covers the cable 92, is rotated, and certain twisting is generated in the cable 92, which is wound on the cable winding drum 93a. Here, this mechanism may be replaced with a mechanism in which the cable winding drum 93a itself is rotated about the axis of the cable 92a which is drawn out from the cable winding drum 93a. With such a mechanism, the occurrence of twisting in the cable 92, which is wound on the cable winding drum 93a, is prevented.

INDUSTRIAL APPLICABILITY

With the first device for inspecting the inside of an underground pipe line of the present invention, the position of the antenna of the radar for inspecting cavities present in the ground surrounding the underground pipe can be varied according to the inner diameter of the underground pipe, so as to become optimum for measurements, and this position can be adapted for inspecting the underground pipes of different inner diameters. Further, because the antenna rotates along the inner peripheral surface of the underground pipe, search for cavities located outside the underground pipe can be conducted over the entire inner peripheral surface of the underground pipe, that is, not only upward of the underground pipe, but also toward both sides and downward thereof.

With the second device for inspecting the inside of an underground pipe line, the rotation center of the antenna is aligned with the center of the inner diameter of the underground pipe. Therefore, uniform search for cavities can be conducted over the entire inner peripheral surface of the underground pipe.

With the third device for inspecting the inside of an underground pipe line, it is possible to create two-dimensional radar images in a plurality of directions outward of the inner peripheral surface of the underground pipe, that is, in a plurality of directions perpendicular to the traveling direction of the self-propelled vehicle inside the pipe line. Further, because the pipe line internal self-propelled vehicle is provided with the antenna position detection means for detecting the position of the antenna, the actual search direction in searching for cavities in the ground around the underground pipe can be accurately associated with a two-dimensional radar image obtained by analyzing the radar signals and the search for cavities can be conducted with good accuracy.

With the fourth device for inspecting the inside of an underground pipe line, the pipe line internal self-propelled vehicle comprises a parallel link mechanism for supporting the antenna, which is positioned on the pipe line internal self-propelled vehicle, so that the antenna can be lifted or lowered according to the height of the ceiling inside the pipe line of the underground pipe. Therefore, the mechanism can be simplified with respect to that in which the antenna is rotated along the inner peripheral surface of the pipe line of the underground pipe.

With the fifth device for inspecting the inside of an underground pipe line, each linkage of the parallel link mechanism has a variable length can be extended and contracted. Therefore, the upper surface of the antenna can follow the ceiling shape and the accuracy of inspection can be improved.

With the sixth device for inspecting the inside of an underground pipe line, there is fixedly provided a fisheye lens camera for taking pictures of the inner peripheral surface of the underground pipe and an expanded image is created from the images picked up with the fisheye lens camera. Therefore, the detailed expanded image of the inner peripheral surface of the underground pipe can be obtained and cracks or fractures of the underground pipe can be detected without using a complex mechanism for rotating the camera.

With the seventh device for inspecting the inside of an underground pipe line or thirteenth device for inspecting the inside of an underground pipe line, the inclination of the underground pipe line or a pattern of cracks or irregularities on the inner peripheral surface of the pipe line can be displayed as a three-dimensional convergence image and the deformation of the inner portions of the underground pipe or cracks and fractures thereof can be detected.

With the eighth device for inspecting the inside of an underground pipe line or fourteenth device for inspecting the inside of an underground pipe line, it is possible to establish the correspondence between the radar image and the expanded image of the same observation point and, when the convergence image is present, to establish the correspondence between the radar image, expanded image and convergence image. Therefore, the position in which a cavity is present can be reliably determined by establishing the correspondence between the position of a specific image on the expanded image or convergence image and the position where the cavity is present on the radar image.

With the ninth device for inspecting the inside of an underground pipe line or fifteenth device for inspecting the inside of an underground pipe line, the distance from the inspection start point of the underground pipe line to the inspection position can be accurately measured and the positions where the cavities or deformations, cracks, and fractures of the underground pipe are present can be reliably determined from the distance from the inspection start point to the position where the cavities or deformations, cracks, and fractures of the underground pipe are present by establishing the correspondence between the measured distance and each of the above-described image.

With the tenth device for inspecting the inside of an underground pipe line or a method for inspecting the deterioration of concrete inside an underground pipe line, a concrete deterioration diagnostic reagent, which colors the surface to which it has adhered into different colors depending on whether concrete deterioration is present or not, is sprayed on the inner peripheral surface of the concrete in the underground pipe line and the results are picked up with the fisheye lens camera. Therefore, the presence of concrete deterioration in the underground pipe line can be judged by the image picked up with the camera.

With the eleventh device for inspecting the inside of an underground pipe line, a reagent for judging the presence of deterioration induced by sulfuric acid is used as the concrete deterioration diagnostic reagent. Therefore, it is possible to judge the presence of concrete deterioration which is induced by sulfuric acid created by the action of sulfur oxidizing bacteria that easily occurs when the underground pipe is a sewage pipe.

With the twelfth device for inspecting the inside of an underground pipe line, the device for inspecting the inside of an underground pipe comprises a sensor for detecting toxic gases such as hydrogen sulfide. Therefore, the presence of toxic gases such as hydrogen sulfide can be inspected simultaneously with the inspection of the underground pipe line.

With the sixteenth device for inspecting the inside of an underground pipe line or a method for inspecting the underground pipe line by using the device, the inspection unit is miniaturized by employing a radar installed on the inspection unit, this radar having a structure such that electromagnetic waves emitted from the antenna thereof are emitted unidirectionally from the outer peripheral surface of the body toward the inner peripheral surface of the underground pipe. Therefore, a device for inspecting the inside of an underground pipe line, which can be used for inspecting underground pipes of small diameter such as lateral sewers connected to the main sewer pipe, and an inspection method using the device can be provided.

Further, a cable is coupled coaxially with the body to the rear portion of the body of the inspection unit, and this cable is covered with a flexible tube having elastic properties. If the cable 2 is pushed or pulled, the body of the inspection unit can be moved forward or backward. Therefore, the inspection unit can be easily moved in the pipe line of the underground pipe.

Further, if the cable is rotated, the body of the inspection unit can be rotated about its axis. Therefore, the inspection of the ground around the underground pipe can be conducted over the entire periphery of the pipe with the radar provided in the inspection unit.

With the seventeenth device for inspecting the inside of an underground pipe line, supporters in the form of semispherical protrusions are provided on the surface of the body of the inspection unit in order to provide for smooth contact between the inspection unit and the inner peripheral surface of the underground pipe during forward or backward movement of the inspection unit or rotation thereof about its axis. Therefore, the inspection unit can be easily moved forward or backward or rotated about its axis.

With the eighteenth device for inspecting the inside of an underground pipe line, the degree of protrusion of the supporters from the outer peripheral surface changes according to changes in the inner diameter of the underground pipe, so that the top portion of the supporters provided at the surface of the body of the inspection unit are in contact with the inner peripheral surface of the underground pipe. Therefore, the central axis of the body of the inspection unit can be aligned with the central axis of the pipe line of the underground pipe and the inspection with the radar can be uniformly conducted over the entire inner peripheral surface of the underground pipe even when the inner diameter of the underground pipe varies. Alternatively, the antenna of the radar can be brought into intimate contact with the inner peripheral surface of the underground pipe even if the inner diameter of the underground pipe varies. Therefore, radar inspection can be conducted with a high accuracy.

With the nineteenth device for inspecting the inside of an underground pipe line, a cable winding unit is used which is provided with a rotation mechanism such that the flexible tube covering the cable can be rotated about its axis. Therefore, the inspection unit can be easily rotated inside the pipe line of the underground pipe.

With the twentieth device for inspecting the inside of an underground pipe line, the inspection unit is provided with a gyro for measuring the rotation axis direction and rotation angle of the inspection unit when the inspection unit rotates about its axis. Therefore, the rotation angle of the inspection unit inside the pipe line of the underground pipe can be easily measured.

With the twenty first device for inspecting the inside of an underground pipe line, there is provided a distance encoder for measuring on the ground the draw-out length of the cable in the insertion direction as the inspection unit is inserted into the pipe line of the underground pipe. Therefore, the position of the inspection unit in the pipe line of the underground pipe can be easily measured.

With the twenty second device for inspecting the inside of an underground pipe line, a fisheye lens camera for taking the pictures of the inner peripheral surface forward in the insertion direction inside the pipe line of the underground pipe is provided at the front end of the inspection unit and an expanded image is created in the on-ground control unit based on the images picked-up with the fisheye lens camera. Therefore, cracks and fractures of the underground pipe can be detected.

The invention claimed is:

1. A device for inspecting the inside of an underground pipe line, which is provided with a radar for inspecting cavities present in at least part of the ground surrounding the underground pipe, the device comprising:
  a pipe line internal self-propelled vehicle, which comprises an antenna for said radar and moves inside the pipe line of said underground pipe; and
  an on-ground control unit for conducting control of said movement of the pipe line internal self-propelled vehicle and processing signals of said radar, wherein
  said pipe line internal self-propelled vehicle comprises an antenna rotation mechanism for rotating said antenna along the inner peripheral surface of said underground pipe and capable of changing the position of said antenna so that said antenna follows said inner peripheral surface.

2. The device for inspecting the inside of an underground pipe line according to claim 1, wherein
  said pipe line internal self-propelled vehicle comprises a height adjustment mechanism capable of changing the position of said antenna rotation mechanism in the up-down direction inside said pipe line of said underground pipe according to the inner diameter of said underground pipe so that the rotation center of said antenna coincides with the center of the inner diameter of said underground pipe.

3. The device for inspecting the inside of an underground pipe line according to claim 1 or 2, wherein said pipe line internal self-propelled vehicle comprises antenna position detection means for detecting the position of said antenna, and
in said on-ground control unit, signals of said radar are analyzed and radar images of the ground surrounding said underground pipe in a plurality of directions perpendicular to the traveling direction of said pipe line internal self-propelled vehicle are created as two-dimensional radar images for each said direction and displayed in a real time mode.

4. The device for inspecting the inside of an underground pipe line according to any one of claims 1 or 2, wherein
  said pipe line internal self-propelled vehicle comprises a gyro for measuring the inclination of said pipe line internal self-propelled vehicle in a traveling direction with respect to the horizontal direction and a laser sensor for rotating along said inner peripheral surface of said underground pipe to measure the convergence of said underground pipe over the entire inner peripheral surface, and the signals of said gyro and the signals of said laser sensor are analyzed in said on-ground control unit to create three-dimensional convergence images and display them in a real time mode.

5. The device for inspecting the inside of an underground pipe line according to any one of claims 1 or 2, wherein said pipe line internal self-propelled vehicle comprises an infrared encoder for measuring the travel distance thereof.

6. The device for inspecting the inside of an underground pipe line according to any one of claims 1 or 2, wherein
  said pipe line internal self-propelled vehicle comprises a fisheye lens camera for taking pictures of said inner peripheral surface of said underground pipe line forward in a traveling direction and the expanded image is created and displayed in a real time mode by said on-ground control unit from the images picked up with the fisheye lens camera.

7. The device for inspecting the inside of an underground pipe line according to claim 6, wherein in said on-ground control unit, the correspondence is established between said radar image and said expanded image in the same observation point or, when said convergence image is present, the correspondence is established between said radar image, said expanded image, and said convergence image in the same observation point.

8. The device for inspecting the inside of an underground pipe line according to claim 6, wherein said underground pipe is made from concrete, and said pipe line internal self-propelled vehicle comprises spraying means for spraying a concrete deterioration diagnostic reagent, which changes the color of the surface to which it has adhered according to the presence or absence of concrete deterioration, on the inner peripheral surface of said concrete in said underground pipe line when said self-propelled vehicle moves inside the pipe line.

9. The device for inspecting the inside of an underground pipe line according to claim 8, wherein a reagent for judging the presence or absence of deterioration caused by sulfuric acid is used as said concrete deterioration diagnostic reagent.

10. The device for inspecting the inside of an underground pipe line according to claim 8, which comprises a sensor for detecting toxic gases such as hydrogen sulfide.

11. The device for inspecting the inside of an underground pipe line according to claim 8, wherein
  said pipe line internal self-propelled vehicle comprises a gyro for measuring the inclination of said pipe line internal self-propelled vehicle in the traveling direction with respect to the horizontal direction and a laser sensor for rotating along said inner peripheral surface of said underground pipe to measure the convergence of said underground pipe over the entire inner peripheral surface, and the signals of said gyro and the signals of said laser sensor are analyzed in said on-ground control unit to create three-dimensional convergence images and display them in a real time mode.

12. The device for inspecting the inside of an underground pipe line according to claim 8, wherein in said on-ground control unit, the correspondence is established between said radar image and said expanded image in the same observation point or, when said convergence image is present, the correspondence is established between said radar image, said expanded image, and said convergence image in the same observation point.

13. The device for inspecting the inside of an underground pipe line according to claim 8, wherein said pipe line internal self-propelled vehicle comprises an infrared encoder for measuring the travel distance thereof.

14. A method for inspecting the deterioration of concrete inside an underground pipe line by using the device for inspecting the inside of an underground pipe line according to claim 8, wherein said spraying means sprays a concrete deterioration diagnostic reagent, which changes the color of the surface to which it has adhered according to the presence or absence of concrete deterioration, on the inner peripheral surface of said concrete in said underground pipe line when said self-propelled vehicle moves inside the pipe line, after said spraying, said fisheye lens camera takes pictures of said inner peripheral surface of said underground pipe line, and said on-ground control unit creates said expanded image from said picked-up images, judges as to whether the deterioration of the inner peripheral surface of said concrete is present based on the expanded image and displays them in a real time mode.

* * * * *